United States Patent
Akers et al.

(10) Patent No.: US 7,144,727 B2
(45) Date of Patent: Dec. 5, 2006

(54) INTERLINKED CULTURE CHAMBER FOR BIOLOGICALS

(75) Inventors: Roger Akers, Houston, TX (US); William J. Anderson, Richmond, TX (US); Stephen S. Navran, Jr., Houston, TX (US)

(73) Assignee: Synthecon, Inc., Houston, TX (US)

( * ) Notice: Subject to any disclaimer, the term of this patent is extended or adjusted under 35 U.S.C. 154(b) by 0 days.

(21) Appl. No.: 10/821,455

(22) Filed: Apr. 9, 2004

(65) Prior Publication Data

US 2004/0203140 A1 Oct. 14, 2004

Related U.S. Application Data

(60) Provisional application No. 60/462,722, filed on Apr. 14, 2003.

(51) Int. Cl.
*C12M 3/06* (2006.01)

(52) U.S. Cl. ............... 435/294.1; 435/297.2; 435/298.2; 210/321.64; 210/257.2; 210/335

(58) Field of Classification Search ............ 435/293.1, 435/293.2, 294.1, 297.2, 297.4, 298.2; 210/321.64, 210/321.78, 321.87, 257.2, 335
See application file for complete search history.

(56) References Cited

U.S. PATENT DOCUMENTS

| | | | |
|---|---|---|---|
| 4,988,623 A | 1/1991 | Schwartz et al. | |
| 5,026,650 A | 6/1991 | Schwartz et al. | |
| 5,104,802 A | 4/1992 | Rhodes et al. | |
| 5,153,131 A | 10/1992 | Wolf et al. | |
| 5,153,133 A | 10/1992 | Schwartz et al. | |
| 5,155,034 A | 10/1992 | Wolf et al. | |
| 5,155,035 A | 10/1992 | Schwartz et al. | |
| 5,194,157 A * | 3/1993 | Ghezzi et al. | 210/646 |
| 5,415,770 A * | 5/1995 | Heskett | 210/202 |
| 5,449,617 A | 9/1995 | Falkenberg et al. | |
| 5,576,211 A | 11/1996 | Falkenberg et al. | |
| 5,637,477 A | 6/1997 | Spaulding et al. | |
| 5,686,301 A | 11/1997 | Falkenberg et al. | |
| 5,763,275 A | 6/1998 | Nagels et al. | |
| 5,998,202 A | 12/1999 | Schwartz et al. | |
| 6,022,733 A | 2/2000 | Tam et al. | |
| 6,080,581 A | 6/2000 | Anderson et al. | |
| 6,255,106 B1 * | 7/2001 | Marx et al. | 435/325 |
| 2004/0110273 A1 * | 6/2004 | Akers et al. | 435/283.1 |

FOREIGN PATENT DOCUMENTS

JP 06134210 A * 5/1994

OTHER PUBLICATIONS

Rai M. et al.; Expression systems for production of heterologous proteins, Current Science, vol. 80, No. 9, May 10, 2001, pp. 1121-1128.

(Continued)

*Primary Examiner*—William H. Beisner
(74) *Attorney, Agent, or Firm*—Elizabeth R. Hall

(57) ABSTRACT

The bioreactor system of the present invention has two fluid-filled culture compartments in which cells, tissues and other biologicals are cultured. The two culture compartments are in fluid communication with each other and each culture compartment is transversed by a filter that prevents the exit of the cells from the culture compartment. Both reusable and disposable culture chambers are described for use as the first and/or second culture compartment.

15 Claims, 12 Drawing Sheets

OTHER PUBLICATIONS

Verma, R. et al.; Antibody engineering: Comparison of bacterial, yeast, insect and mammalian expression systems, Journal of Immunological Methods, 216, 1998, pp. 165-181.

Hernaeus Instruments, Inc.; Genetic Engineering News, vol. 14, No. 12, Jun. 15, 1994.

FiberCell Hollow Fiber Cell Culture Systems, Dec. 1, 2004 printout, Internet at bellcoglass.com.

Gerecht-Nir, Sharon, et al. Bioreactor cultivation enhances the efficiency of human embryoid body (hEB) formation and differentiation, Biotechnology and Bioengineering, Early view online Apr. 8, 2004.

* cited by examiner

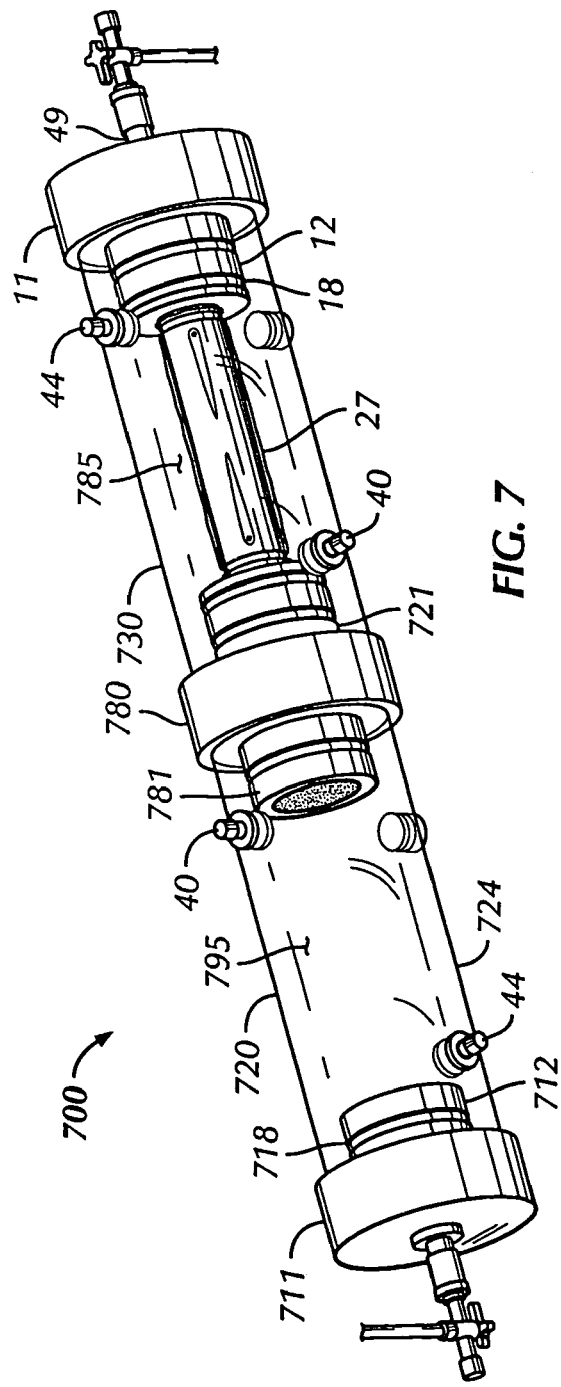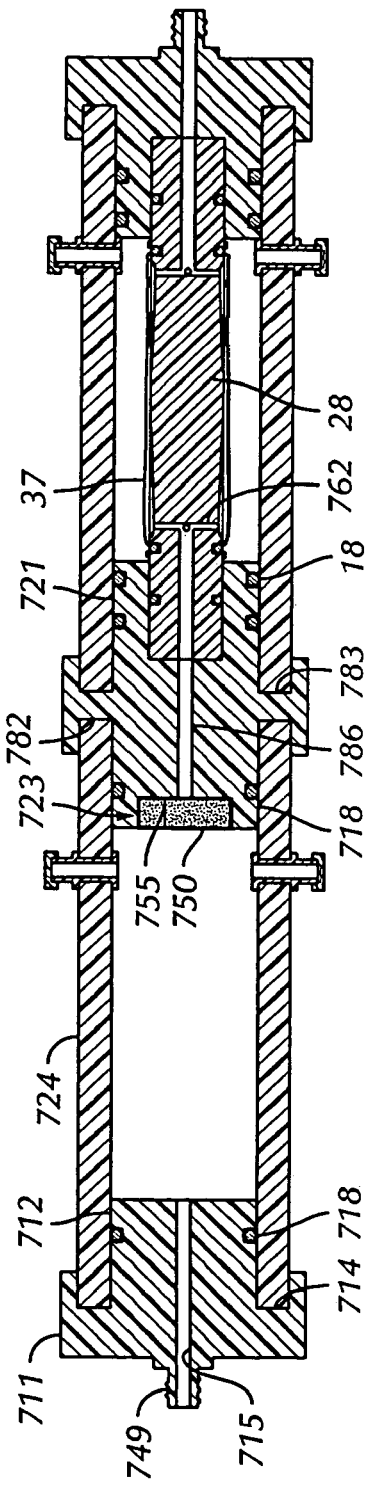

INTERLINKED CULTURE CHAMBER FOR BIOLOGICALS

CROSS REFERENCE TO RELATED APPLICATIONS

This application claims priority to pending U.S. patent application Ser. No. 60/462,722 filed Apr. 14, 2003 by inventors Roger Akers, William Anderson, and Stephen Navran, Jr. and entitled "Interlinked Culture Chambers for Biologicals." The entire text of the above-referenced disclosures is incorporated by reference herein.

BACKGROUND OF THE INVENTION

1. Field of the Invention

The present invention relates to a culture chamber for culturing cells, cellular aggregates, particles, tissues and organoids that respond to secretions from other cells, cellular aggregates, particles, tissues and organoids. More particularly, the present invention relates to a culture chamber having a first set of one or more biological culture chambers interconnected with a second set of one or more other biological culture chambers, wherein the secretions of the first set of biological culture chambers is fed into the second set of biological culture chambers.

2. Description of the Related Art

A variety of cell lines, including human embryonic stem (HES) cells require hormones, growth factors or other materials that are secreted from another cell type (commonly referred to as feeder cells). The therapeutic potential of such cells is only beginning to be realized. To keep pace with the ever increasing demand for the potential presented by such cells, new processes and apparatuses are needed that can efficiently provide a first set of cells with the secretions from another set of cells.

One of the major problems in the production of cells and cellular products is the required cleaning, sterilization and validation of the standard stainless steel or glass bioreactors by the customer. Furthermore, none of the currently available culture chambers are designed to have secretions of one culture chamber feed into another culture chamber.

Thus, a need exists for disposable culture chambers having a reduction in the risk of cross contamination and the downtime needed for equipment changeover between production runs.

In addition, a need exists for a simplified, efficient means of interlinking culture chambers such that one can culture one cell and transfer that cell's secretions into the media used to grow another cell type.

SUMMARY OF THE INVENTION

The invention contemplates a culture chamber having a first set of one or more biological culture chambers interconnected with a second set of one or more other biological culture chambers, wherein the secretions of the first set of biological culture chambers is fed into the second set of biological culture chambers. The present invention includes a serially arranged culture chamber system having separate but closely interconnected fluid-filled chambers in which cells, tissues and other biologicals are cultured without intermingling and wherein first, upstream chambers provide growth factors or precursor compounds for the second, downstream chambers.

Each of the upstream culture chambers is either traversed by one or more molecular weight cut-off membranes or provided with outlet filters that serve to separate the cells of an upstream chamber from the other, downstream flow-streams and chambers.

One aspect of the invention is a culture system comprising: (a) a fluid inlet; (b) a first culture compartment having a tubular housing; (c) a first end piece attached to the fluid inlet on one side and to a first end of the tubular housing on a second side, (d) a second culture compartment coaxial with the first culture compartment, the second culture compartment having a proximal end and a distal end; (e) a fluid connector having a first side mounted on a second end of the tubular housing and a second side mounted on the proximal end of the second culture compartment, the fluid connector having a through bore passing from the first side to the second side of the fluid connector; (f) a connector filter positioned on the first side of the fluid connector to filter a fluid stream passing out of the first culture compartment and into the through bore of the fluid connector; (g) a fluid outlet; (h) a distal end piece mounted on the distal end of the second culture compartment and connected to the fluid outlet; and (i) an outlet filter supported by the distal end piece.

Another aspect of the invention is a culture system comprising: (a) a fluid inlet; (b) a first culture compartment having (i) a tubular sleeve, (ii) a growth compartment within the sleeve, (iii) a first end piece attached to the fluid inlet on one side and to a first end of the tubular housing on a second side, and (iv) a membrane carrier assembly transversing the growth compartment comprising a support cylinder, a molecular weight cut-off membrane secured to an exterior surface of the support cylinder, and a chamber between the exterior surface of the cylinder and an interior surface of the membrane, the chamber in fluid communication with the fluid inlet and the growth compartment; (c) a second culture compartment coaxial with the first culture compartment, the second culture compartment having a proximal end and a distal end; (d) a fluid connector having a first side mounted on a second end of the tubular sleeve and a second side mounted on the proximal end of the second culture compartment, the fluid connector having a through bore passing from the first side to the second side of the fluid connector wherein the through bore is in fluid communication with the chamber of the membrane carrier assembly and the interior of the second culture compartment; (e) a fluid outlet; (f) a distal end piece mounted on the distal end of the second culture compartment and connected to the fluid outlet; and (g) an outlet filter supported by the distal end piece.

Yet another aspect of the present invention is a culture system comprising: (a) a fluid inlet; (b) a first culture compartment having a tubular housing; (c) a first end piece attached to the fluid inlet on one side and to a first end of the tubular housing on a second side, (d) a second culture compartment coaxial with the first culture compartment, the second culture compartment having a proximal end and a distal end; (e) a fluid connector having a first side mounted on a second end of the tubular housing and a second side mounted on the proximal end of the second culture compartment, the fluid connector having a through bore passing from the first side to the second side of the fluid connector; (f) a connector filter positioned on the first side of the fluid connector to filter a fluid stream passing out of the first culture compartment and into the through bore of the fluid connector; (g) a fluid outlet; (h) a distal end piece mounted on the distal end of the second culture compartment and connected to the fluid outlet; and (i) an outlet filter transversing the second culture compartment including: a support cylinder having a first end supported by the fluid connector and a second end supported by the distal end piece, a molecular weight cut-off membrane secured to an exterior surface of the support cylinder, and a chamber between the exterior surface of the cylinder and an interior surface of the membrane, the chamber in fluid communication with the through bore of the fluid connector and the fluid outlet.

Still yet another aspect of the present invention is a culture system comprising: (a) a fluid inlet; (b) a first culture compartment having a tubular housing; (c) a first end piece attached to the fluid inlet on one side and to a first end of the tubular housing on a second side, (d) a fluid connector having a first side mounted on a second end of the tubular housing, the fluid connector having a through bore passing from the first side to a second side of the fluid connector; (e) a connector filter positioned on the first side of the fluid connector to filter a fluid stream passing out of the first culture compartment and into the through bore of the fluid connector; (f) a culture bag including a flexible external wall having a first end, a second end, an internal side, and an external side, wherein the internal side of the external wall is positioned to face an interior of the culture bag, a first bag end fused to the first end of the external wall and attached to the second side of the fluid connector, a second bag end fused to the second end of the external wall, and an outlet filter supported by the second bag end; and (g) a fluid outlet.

Yet another aspect of the present invention is a culture system comprising: (a) a fluid inlet; (b) a first culture bag having a flexible external wall having a first end, a second end, an internal side, and an external side, wherein the internal side of the external wall is positioned to face an interior of the first culture bag, a first bag end fused to the first end of the external wall and attached to the fluid inlet, a second bag end fused to the second end of the external wall, and a first bag filter positioned on the second bag end to filter a fluid stream passing out of the first culture bag; (c) a fluid connector having a first side mounted on the second bag end, the fluid connector having a through bore passing from the first side to a second side of the fluid connector; (d) a second culture bag including a flexible outer wall having a first end, a second end, an internal side, and an external side, wherein the internal side of the outer wall is positioned to face an interior of the second culture bag, a proximal bag end fused to the first end of the outer wall and attached to the second side of the fluid connector, a distal bag end fused to the second end of the outer wall, and an outlet filter supported by the distal bag end; and (g) a fluid outlet.

The foregoing has outlined several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiments disclosed might be readily utilized as a basis for modifying or redesigning the method or process for carrying out the same purposes as the invention. It should be realized that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 7 shows an oblique view of one embodiment of interconnected culture chambers of approximately equal capacity;

FIG. 8 is a longitudinal cross-sectional view of the interconnected culture chambers of FIG. 7;

DESCRIPTION OF THE PREFERRED EMBODIMENTS

Figure 1:
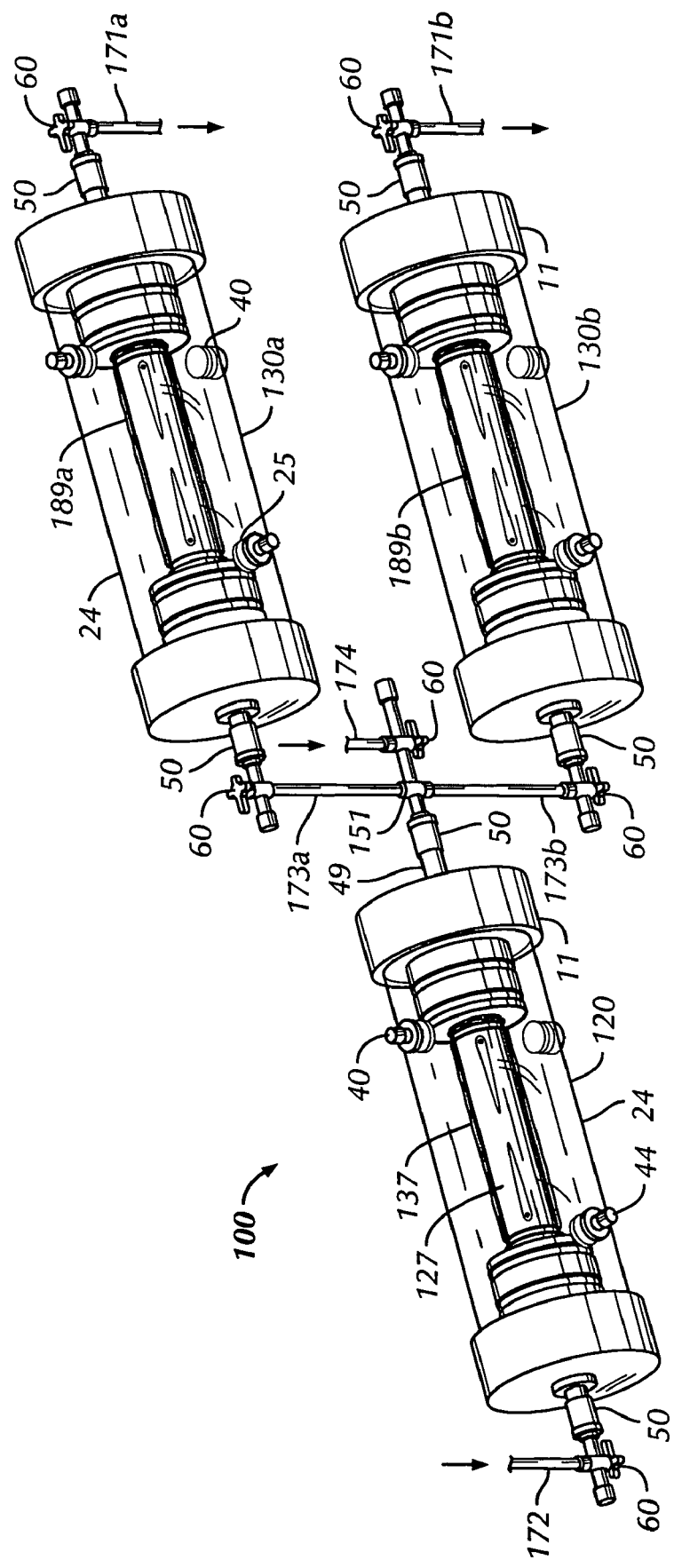
FIG. 1 shows an oblique view of interlinked culture chambers.

The interlinked culture chambers of the present invention are designed for culturing cells, cellular aggregates, particles, tissues and organoids that respond to secretions from other cells, cellular aggregates, particles, tissues and organoids. The tandem culture chamber of the present invention has a first set of one or more biological culture chambers interlinked with a second set of one or more other biological culture chambers, wherein the secretions of the first set of biological culture chambers are fed into the second set of biological culture chambers without the intermingling of cells. Both reusable and disposable culture chambers are described for culturing cells, cell aggregates, particles, tissues and organoids.

The serially arranged culture chambers of the present invention have fluid-filled culture compartments in which cells, tissues and other biologicals are cultured. The walls of the chambers can be either rigid or a flexible bag-like construction. Normally, the bag construction is used in disposable applications in order to minimize possibilities of cross contamination between culture lots. Examples of suitable disposable bag-like chambers are described in U.S. Pat. No. 6,673,598 B1 issued on Jan. 6, 2004 and entitled "Disposable Culture Bag", which is hereby incorporated herein by reference. Examples of suitable rigid and bag-like chambers are described in U.S. patent application, Ser. No. 10/725,607 filed Dec. 2, 2004 and entitled "Culture Chamber for Biologicals", which is hereby incorporated herein by reference.

In addition, either the rigid chamber or the bag system may use either a controlled molecular weight cut-off membrane structure or a controlled permeability filter to separate the culture media and the cells in the chamber from the outflow fluid. When a molecular weight cutoff membrane is used, certain constituents of the fluids on both sides of the membrane can diffuse across the membrane, so a properly constituted membrane can function to separate components of the biological media within the chamber from its outflow stream. When a suitably constructed outlet filter is positioned at the upstream end of the outlet end piece flow channel for a bioreactor chamber, the filter serves to prevent the cells and/or large particulate constituents of the biological media from passing through the filter into the outflow stream.

Different types of chambers may be used within an individual serially arranged culture system. For example, a rigid cell first chamber may be best suited for the preparation of a growth hormone, required nutrient, or precursor molecule needed for the well being of the cells in a disposable second chamber or vice versa. Interconnectors are described that allow multiple permutations of one or more rigid or flexible disposable culture chambers of a first set of chambers to be interlinked with one or more rigid or flexible disposable culture chambers of a second set of chambers.

The culture chambers of the present invention are generally configured so that they can be slowly rotated and provided with optimal conditions for the promotion of cell growth. The mechanisms for rotation of the bioreactors are not shown herein, but the details of the bioreactor chambers related to providing this rotational capability are shown. Accordingly, an example of an inlet and outlet fluid coupling swivel joint is described.

Interlinked Reusable Bioreactor Systems

The tandem culture chamber of the present invention has a first set of one or more biological culture chambers, hereinafter referred to as feeder cell chambers, interlinked with a second set of one or more other culture chambers. Reusable cell culture chambers are often desired to investigate a variety of systems for the production of a particular product and for optimizing certain growth parameters. Reusable cell culture chambers are typically made of a rigid plastic material that is non-toxic and non-reactive with biological systems, as well as being sterilizable.

The feeder cell chamber of the present invention has a fluid-filled culture compartment in which cells, tissues and other biologicals are cultured. The culture compartment is transversed by one or more molecular weight cut-off membranes attached to a membrane carrier assembly or provided with outlet filters to prevent the cells from leaving the culture compartment. Incoming nutrients and/or biological modifiers are transported through the membrane into the culture compartment and secretions (such as hormones, growth factors, differentiation factors, and metabolic waste products) are transported away from the fluid-filled culture compartment through the membrane and out the chamber outlet.

Referring now to the drawings, and initially to FIG. 1, it is pointed out that like reference characters designate like or similar parts throughout the drawings. The Figures, or drawings, are not intended to be to scale. For example, purely for the sake of greater clarity in the drawings, wall thickness and spacing are not dimensioned, as they actually exist in the assembled embodiment. In the Figures used to describe the interlinked culture chambers the media flows from the left to the right. Thus, the first set of one or more chambers (i.e., the feeder cell chambers) is positioned on the left and the second set of chambers is positioned on the right.

EXAMPLE 1

Interlinked Reusable Culture Chambers

FIG. 1 illustrates the interlinking of a number of reusable culture chambers. Although numerous permutations of such arrangements are possible, FIG. 1 shows an arrangement connecting three separate rigid bioreactor vessels of the type described in detail in pending U.S. patent application, Ser. No. 10/725,607, entitled "Culture Chamber for Biologicals."

The first chamber 120 utilizes a first molecular cutoff membrane 137 and is upstream of the two bioreactors 130a,b of the second chamber set. The first chamber 120 produces a desired growth hormone or other growth mediator for supply to the second chamber set 130a,b. This arrangement is utilized when the cells grown in one bioreactor chamber 120 are able to provide sufficient growth hormone, precursor, or component to contribute to the growth of cells in multiple second bioreactor chambers 130a,b. The second bioreactors 130a,b may have the same cell line or different cell lines.

Each of the bioreactor chambers 120, 130a,b is rotated. A variety of drive assemblies may be used to rotate the culture chamber such as the drive assembly described in U.S. Pat. No. 6,080,581. The arrangement of the rotational equipment can be multiple independent sets of the standard rotators known to those in the industry, or alternatively a gang rotation system could be used. The bioreactor chambers 130a,b are rotated substantially the same to generate a similar, balanced environment for the chambers. The two bioreactors of the second chamber set are similar to each other and use a second and third molecular cutoff membrane 189a,b optimized for the cells being cultured in the bioreactors and for the products being produced by the second chamber set.

Figure 2:
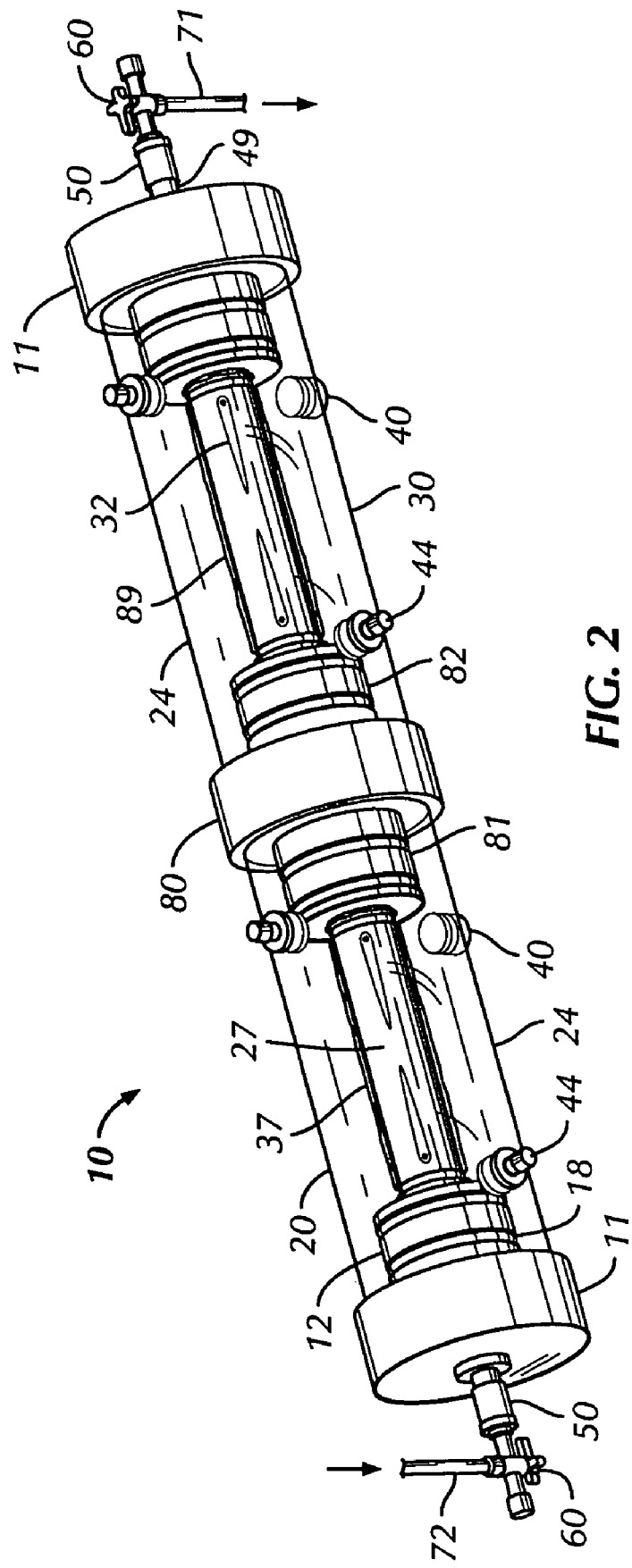
FIG. 2 shows an oblique view of one embodiment of interconnected culture chambers of approximately equal capacity.
Figure 3:
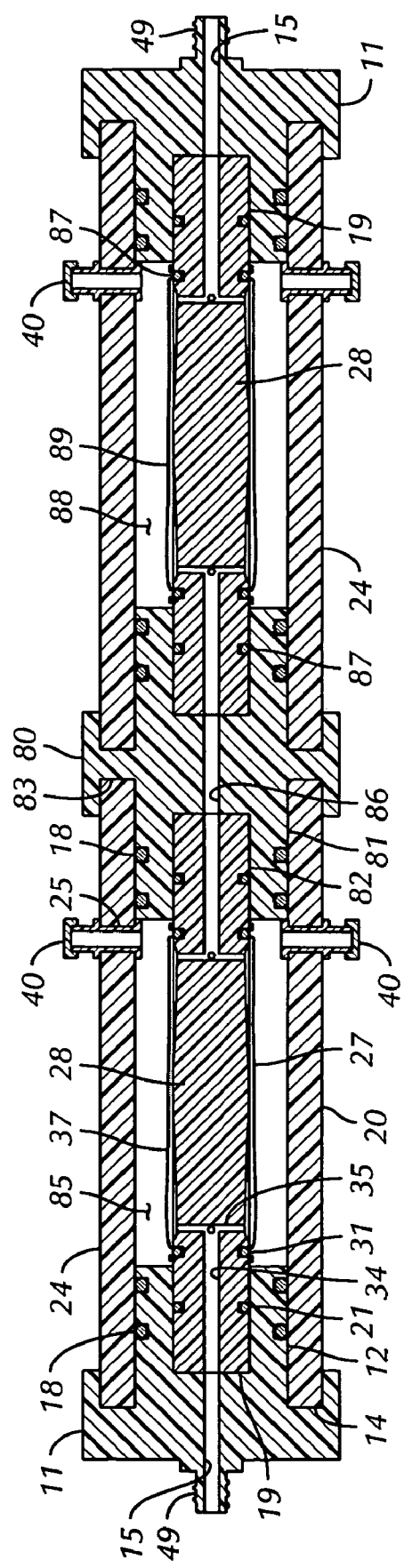
FIG. 3 is a longitudinal cross-sectional view of the interconnected culture chambers of FIG. 2.

All three bioreactors shown in FIG. 1 are constructed of the same components except for their respective membranes and have most components in common with those used in the interconnected culture chambers shown in FIG. 2 and described in more detail in Example 2. Thus, each chamber has an end piece 11 sealingly engaged on each end of a sleeve 24 and also has a membrane carrier assembly 127, located axially within the interior of sleeve 24, thereby forming a bioreactor chamber. The sleeve 24 has multiple radial wall penetration ports 25, as shown in FIG. 3. These penetration ports 25 are provided in the annular wall of sleeve 24 to allow the introduction of one or more fill ports 40 and one or more samplingports 44.

The biologicals being cultured in the rotatable chambers 120 and 130a,b require nutrients, so fluid-conducting swivels 50, stopcock valves 60, intermediate tubings 173a,b and fluid inlet tubing 172 and outlet tubing 171a,b are provided for the system. The system 100 is plumbed so that nutrient fluid enters the first chamber 120 of the system through inlet tubing 172, stopcock 60, and swivel 50. The fluid output from chamber 120 emerges through attachment neck 49 and swivel 50 of the outlet side endpiece 11 of the first chamber 120.

The flow then passes to a fluid conducting cross fitting 151 which has connections to both the two bioreactor chambers 130a,b via identical intermediate tubings 173a,b and which also connects to another stopcock 60. The intermediate tubings 173a,b are identical in order to ensure the balanced flow of nutrients to the second set of chambers. The stopcock 60 on the cross fitting 151 is attached to secondary fluid feed line 174 which can be used to supplement or alter the fluid mixture delivered to the second chambers 130a,b. The outflow from each of the second chambers passes through a swivel 50, stopcock 60, and outlet tubings 171a,b. This arrangement permits full control of the fluid system for the bioreactors of system 100.

EXAMPLE 2

Interconnected Equal Capacity Culture Chambers

FIG. 2 shows two interconnected bioreactors similar to the bioreactors described in Example 1. The particulars of the construction of the components of culture chamber 10 are best understood with reference to FIGS. 2–3. The serially arranged bioreactor system 10 is composed of two individual reusable rigid walled bioreactor chambers 20 and 30 cojoined by a fluid connector or center hub piece 80.

The first bioreactor chamber 20 is located on the inlet side and serves to feed the second bioreactor chamber 30. The media flows from the left to the right in the Figures. The biologicals being cultured in the rotatable chambers 20 and 30 require nutrients, so fluid-conducting swivels 50, stopcock valves 60, and fluid inlet tubing 72 and outlet tubing 71 are provided on the ends of the tandem housing 10 so that the entry and exit of media is controlled.

For first bioreactor chamber 20, an end piece 11 seals to the upstream end of right circular cylindrical tubular sleeve 24 and center hub 80 seals to the downstream end so that a growth compartment 85 is formed within the enclosed space. When in use for culturing cells, cellular aggregates, particles, tissues and organoids, the culture chamber is designed to be supported on and rotated by a roller drive which rotates the chamber about its axis. In this situation, the end pieces 11 and the center hub 80 serve as tires for contact of the assembly 10 with the drive wheels of the drive assembly. A variety of drive assemblies, not shown here, may be used to rotate the culture chamber such as the drive assembly described in U.S. Pat. No. 6,080,581.

Multiple radial wall penetration ports 25 are provided in the annular wall of sleeve 24 to allow the introduction of one or more fill ports 40 and one or more samplingports 44. The swivel 50, the fill port 40, and the samplingport 44 are described in more detail in U.S. Pat. No. 6,673,598 B1 that is incorporated herein by reference.

End piece 11 has a right circular cylindrical central body having a coaxial push-on hose barb attachment neck 49 on its outer face. Axial through hole 15 penetrates through the attachment neck 49 and the rest of the body of end piece 11. Reduced diameter coaxial right circular cylindrical interior projection 12 extends inwardly on the transverse face of the interior end of end piece 11, with a flat-bottomed trepanned groove 14 located on the transverse interior face of end piece 11 immediately exterior of projection 12.

The exterior cylindrical surface of interior projection 12 has annular male O-ring grooves. Elastomeric O-rings 18 are mounted in the O-ring grooves of projection 12. At the interior end of interior projection 12 of end piece 11, flat-bottomed coaxial counterbore 19 intersects through hole 15. An optional lead-in chamfer may be provided at the mouth of counterbore 19 in order to facilitate the stabbing of an O-ring seal with the membrane carrier assembly.

The right circular cylindrical sleeve 24 can be made of a variety of materials such as glass, stainless steel or plastic. Preferably the reusable cell culture chamber is constructed of plastic, typically a transparent plastic such as an acrylic plastic for the cylindrical sleeve 24 and opaque plastics such as Kynar™ or Delrin™ for the other rigid pieces such as the end pieces 11. Suitable plastics have substantially zero porosity and are impermeable to gases and non-reactive to biological media and its components. Suitable construction materials must also be able to undergo multiple sterilizations by steam, gas, or radiation without deforming, cracking or otherwise being rendered unusable.

Although not shown in FIG. 3, the right circular cylindrical sleeve 24 is preferably provided with a lead-in taper on each of its interior corners to facilitate the stabbing of O-rings 18 over the interior projections 12 and 81 forming the ends of first chamber 20. The interior bore of sleeve 24 is a close sliding fit to the outer diameter of interior projection 12 of end fitting 11, thereby permitting O-rings 18 to sealingly engage the bore of sleeve 24. O-rings 18 also serve to retain sleeve 24 in its desired axial position by virtue to their forceful frictional engagement with sleeve 24.

As previously stated, the sleeve 24 has multiple radial wall penetration ports 25 to allow the mounting of fittings used for inserting fluid into or removing fluids from the growth compartment 85 and for allowing gas to escape from the growth compartment 85 as it is being filled with fluid. At each end of chamber 20, sleeve 24 is stabbed over the interior projections 12 and 81 and bottomed out in the trepanned grooves 14 and 83 at the interior ends of end piece 11 and center hub 80, respectively. The growth compartment 85 is located between the interior bore of the sleeve 24, the membrane carrier assembly 27, the interior end of interior projection 12 of end piece 11, and the interior end of the interior projection 81 of the center hub piece 80.

Center hub 80 is a structure composed of cylindrical segments and is symmetrical about its transverse midplane. Center hub 80 has an axial through hole 86 that provides communication from one side of the piece to the other, so that center hub 80 not only supports chambers 20 and 30, but also provides a flow connection between the chambers 20 and 30. The interior projection 81 of center hub 80 is identically structured to projection 12 of end piece 11 and carries two male O-ring grooves that hold O-rings 18. The O-rings 18 mounted in the grooves of center hub 80 sealingly mate with and restrain the axial position of cylindrical sleeve 24.

A membrane carrier assembly 27, as shown in FIGS. 2 and 3, traverses the growth compartment 85. An end of the generally cylindrical membrane carrier assembly 27 is mounted in the counterbores 19 and 82 of each of the two end assemblies 11 and 81, respectively, used in chamber 20.

FIG. 3 shows the details of construction of membrane carrier assembly 27. Support cylinder 28 is symmetrical about its transverse midplane. The exterior of each end of cylinder 28 has, sequentially from its end, a lead-in taper to ease blind stabbing into a mounting hole, a first annular male O-ring groove 21 mounting elastomeric O-ring 87, and a second groove 31 configured similarly to an O-ring groove and used to mount a second O-ring 87, wherein the second O-rings serve to sealingly grip their respective ends of the membrane 37 which is deployed around the support cylinder 28. Each end of cylinder 28 also has an axial blind hole 34 with multiple (in this case, four) equispaced coplanar radial cross holes 35 intersecting the inner end of blind hole 34.

A small recessed surface pocket 32 having an arcuate cross-section is located on the exterior of cylinder 28 and is intercepted by each radial cross hole 35. The depth of these surface pockets 32 below the outside cylindrical diameter is largest near the intersection with its cross hole 35 and linearly tapers to zero towards the middle of cylinder 28.

Centrally deployed with a close fit around the exterior of cylinder 28 is a tubular molecular weight cut-off membrane 37. Membrane 37 is flexible with a limited amount of elastic stretch capability. The construction of membrane 37 is very carefully controlled so that the number of molecules, having a molecular weight in excess of the specific limiting molecular weight cut-off value of the membrane 37, diffused through the membrane in either direction is statistically very small and rapidly decreases as a function of increasing molecular weight. Thus, there is essentially no passage of molecules much larger than the molecular weight cut-off value of the membrane through the membrane 37.

The molecular weight cut-off value of the membrane 37 is preselected so that nutrients and growth factors, as well as metabolic waste products, can easily diffuse through the membrane, whereas larger cellular products can be retained. For example, Factor VIII (having a molecular weight of about 350,000 daltons) or IgG monoclonal antibodies (having a molecular weight of about 155,000 daltons) produced by genetically engineered bacteria or cells can be retained by a membrane with a molecular weight cut-off value of about 100,000 daltons; whereas the majority of serum albumin (having a molecular weight of about 67,500 daltons and making up 55% to 62% of serum protein) would be allowed to pass through the membrane. Since the culture chamber 20 is reusable, the membrane carrier assembly 27 can be assembled with membranes 37 having a variety of molecular weight cut-off values depending on the desired secretions being produced. The membrane 37 is selected to allow the user to select a molecular weight cut-off value that would allow the desired protein or other cell secretions to serve as feedstock or stimulant for the cells in the second bioreactor chamber 30.

As shown in FIG. 3, membrane 37 is sealed to the exterior of cylinder 28 at each end by using an O-ring 87 to circumferentially constrict over the exterior of membrane 37, thereby forcing it into sealing engagement with groove 31 on the outside of cylinder 28. In this manner, a small chamber in fluid connection with the radial flow passage 35 is formed between the exterior of surface pockets 32 and the interior of membrane 37. The depth and length of cut for the surface pockets 32 is predetermined to be sufficient to produce a sufficient pressure area so that the elastic resistance of membrane 37 can be overcome. The expansion of the membrane 37 when media is passed through flow passage 35 and along the surface pockets 32 of support cylinder 28 permits a thin flow sheet of media between the membrane 37 and cylinder 28 to be established.

Second chamber 30 is a mirror image of first chamber 20 except that the membrane 89 is used in place of membrane 37 in the assembly of the membrane carrier assembly 27. Membrane 89 is preselected for its molecular weight cut-off value according to desires of the user. The influx of fluid emerging from first chamber 20 and into the membrane carrier assembly 27 has its desired components diffusing across the membrane 89 into volume 88 for reaction with the cells therein. However, the bioactive fluid within the volume 88 has waste products from the tandem cell arrangement of serial bioreactor 10 transfusing across membrane 89 and into the outflow stream of chamber 30 to emerge through hole 15 in end piece 11 and thence to fluid outlet tubing 71.

The present invention allows the user to select a membrane having a molecular weight cut-off value that would allow the desired protein or cellular product to pass out of the culture chamber with the waste products for collection and purification. However, the present invention also permits the user to select a membrane having a smaller molecular weight cut-off value than the desired protein or cellular product, so that the desired product is retained within the culture chamber and is concentrated with time as the cells multiply and continue to produce the desired product. Since the culture chamber 10 is reusable, the membrane carrier assemblies 27 can be assembled with membranes 37 and 89 having a variety of molecular weight cut-off values depending on the user's needs.

EXAMPLE 3

Interconnected Culture Chambers of Different Capacities

The interconnected culture chambers 10, as shown in FIGS. 2 and 3, may be configured where either chamber is shorter than the other chamber thereby interconnecting culture chambers of different capacities but having a hub 80 that joins chambers of substantially the same internal diameter.

Figure 4:
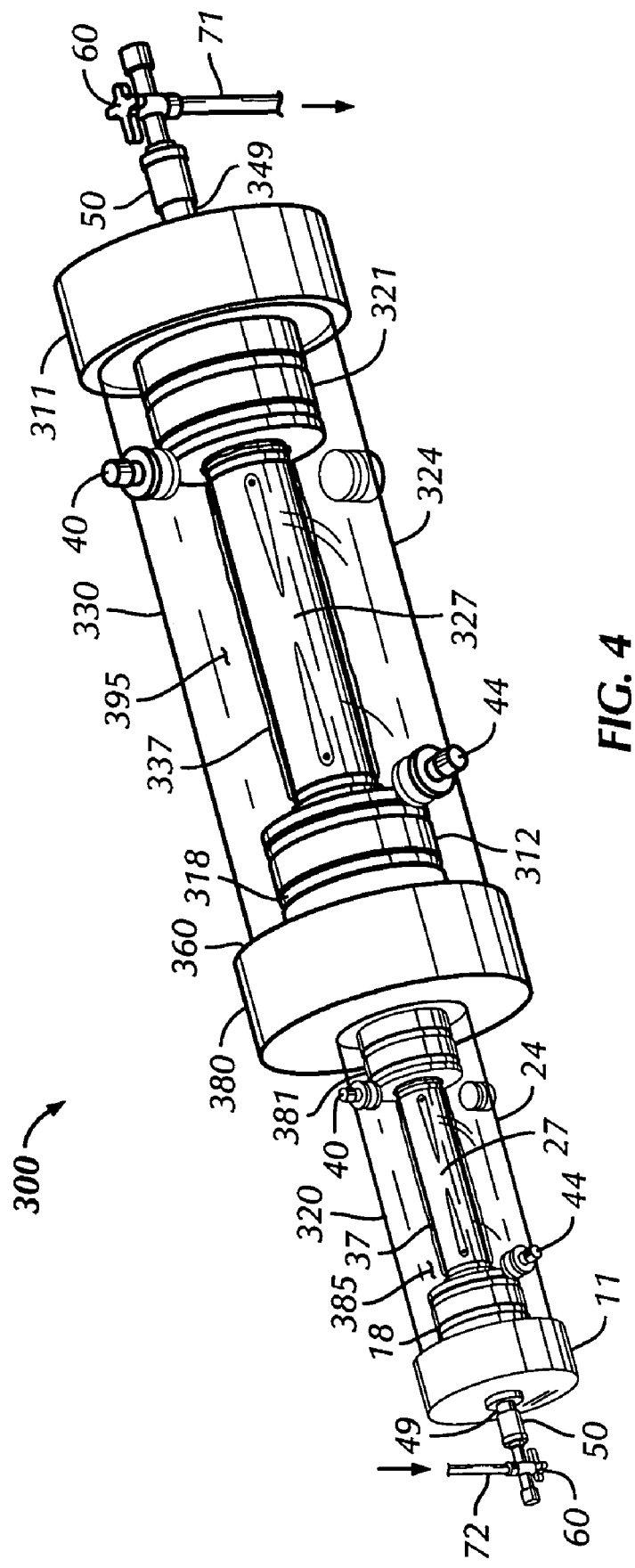
FIG. 4 shows interconnected culture chambers where the chambers have different capacities and the larger chamber has a single diffusion membrane positioned within its interior.

Alternatively, the interconnected culture chambers 300, illustrated in FIG. 4, represent an embodiment of the serially arranged bioreactor system having culture chambers of different capacities. This bioreactor system utilizes basically the same arrangement as is used for the bioreactor system 10, except that the second chamber is a different size either in diameter and/or in length than the first chamber.

This arrangement basically utilizes two rigid coaxial bioreactor vessels 320 and 330 cojoined in tandem. The first chamber 320 utilizes a first molecular cutoff membrane 37 and is upstream of the bioreactor 330 of the second chamber. One of the features of this embodiment is the large size of second chamber 330 relative to first chamber 320. This arrangement is utilized when the first bioreactor chamber 320 is able to provide sufficient growth hormone or stimulator for a single large second bioreactor chamber 330.

The cojoined bioreactor chambers 320 and 330 are rotated as an unit using standard rotational equipment known to those in the industry, but with three supporting drive rollers which act on the tires of the end pieces 11 and 311 and the center hub 380.

The first chamber 320 produces a growth factor or other mediator for supply to the second chamber 330. The bioreactor of the second chamber uses a second molecular cut-off membrane 337 that is optimized for its cells and the outputs desired from the second chamber.

The first bioreactor chamber 320 of the system embodiment 300 has all of its components including the input fluid system in common with that of the first chamber 20 of the interconnected culture chambers 10 of the present invention, except that a different fluid connector or center hub 380 is used. Thus, first chamber 320 has an end piece 11 sealingly engaged on the inlet end of a sleeve 24 and also has a membrane carrier assembly 27 located axially within the interior of sleeve 24, thereby forming a bioreactor chamber as before. Multiple radial wall penetration ports 25 are provided in the annular wall of sleeve 24 to allow the introduction of one or more fill ports 40 and one or more samplingports 44.

The biologicals being cultured in the rotatable chambers 320 and 330 require nutrients, so fluid-conducting swivels 50, stopcock valves 60, fluid inlet tubing 72, and outlet tubing 71 are provided for the system. The system 300 is plumbed identically to that of the interconnected culture chambers of the bioreactor system 10 so that nutrient fluid enters the first chamber 320 of the system through inlet tubing 72, stopcock 60, and swivel 50. The fluid output from chamber 320 passes through a hole in center hub 380 into the second bioreactor chamber 330. The outflow from the second chamber 330 passes through a swivel 50, stopcock 60, and outlet tubing 71.

The growth compartment 385 of the first chamber 320 is located between the interior bore of the sleeve 24, the membrane carrier assembly 27, the interior end of interior projection of end piece 11, and the interior end of the interior projection 381 of the center hub piece 380.

Center hub 380 is a structure composed of right circular cylindrical segments. Center hub 380 has its first side on the first chamber side of its transverse midplane identical to the corresponding side of center hub 80 of the bioreactor system 10 and likewise identical to the end piece 11 of the first chamber 320 with hose barb attachment neck 49 removed. The first interior projection 381 of center hub 380 carries two male O-ring grooves that hold O-rings 18. The O-rings 18 mounted in the grooves of the interior projection of center hub 380 also sealingly mates with and restrains the axial position of cylindrical sleeve 24. Furthermore, the external cylindrical portion of hub 380 adjacent the interior projection serves as a tire for the rotation of the entire bioreactor assembly 300.

On its first side center hub 380 has a flat-bottomed cylindrical bore for housing the membrane carrier assembly 27 of the first chamber. On its second side obverse to the said first side of center hub 380 and in order from the transverse midplane of center hub 380 is a cylindrical flange 360 and a second projection 312 into the second chamber 330. The flange 360 is the same diameter as, or slightly larger than sleeve 324, used for the second chamber 330. The second interior projection 312 is sized to closely fit to the bore of sleeve 324 and has two male O-ring grooves mounting O-rings 318 to seal therewith.

An axial through hole provides communication from the counterbore on the first side of the hub 380 to a similar axial counterbore on the opposed side of hub 380. Optional lead-in chamfers are provided at the mouth of these counterbores in order to facilitate the stabbing of an O-ring seal with the membrane carrier assembly 327. Thus hub 380 not only supports chambers 320 and 330 but also provides a flow connection for the chambers.

Sleeve 324 is similar in construction to that of sleeve 24 used with the first chamber 320, but differs only in its inner and outer diameters. The inner diameter of sleeve 24 is chosen to be sufficient to accommodate the membrane carrier assembly 327 and provide sufficient volume for chamber 330. The outer diameter is selected for strength and rigidity. As is the case for sleeve 24, sleeve 324 has wall penetrations for the mounting of multiple fill ports 40 and samplingports 44. Sleeve 324 is a close fit to second inner projection 312 of center hub 380.

End piece 311 has a right circular cylindrical central body having the same outer diameter as the enlarged flange having a coaxial push-on hose barb attachment neck 349 on its outer face. A reduced diameter coaxial right circular cylindrical interior projection extends inwardly on the transverse face of the interior end of end piece 311, with a transverse shoulder located on the transverse interior face of end piece 311 immediately exterior of the projection. The exterior cylindrical surface of the interior projection 321 has annular male O-ring grooves. Elastomeric O-rings 318 are mounted in the O-ring grooves of projection 321. An axial through hole penetrates through attachment neck 349 and the rest of end piece 311, where it centrally intercepts a counterbored flat bottom hole to form a flow path for the fluid exiting from the second chamber 330. Optional lead-in chamfers are provided at the mouth of the counterbore in order to facilitate the stabbing of an O-ring seal with the membrane carrier assembly 327.

A membrane carrier assembly 27 as shown in FIG. 4 for this bioreactor system 300 traverses the growth compartment 385. An end of the generally cylindrical membrane carrier assembly 27 is mounted in the counterbores of each of the two assemblies 11 and 380, respectively, forming the end of compartment 385 used in chamber 320.

A membrane carrier assembly 327 as shown in FIG. 4 traverses the growth compartment 395 of the second chamber 330. The membrane carrier 327 is substantially identical to the unit used in the first chamber 385 and the prior embodiments 10 and 100 of the present invention, but membrane carrier 327 is much larger and mounts a different molecular cutoff membrane 337 that is optimized for the cell growth in the second chamber 330. An end of the generally cylindrical membrane carrier assembly 327 is mounted in the counterbores of each of the two chamber end pieces 311 and 380, respectively, forming the end of compartment 395 used in chamber 330.

EXAMPLE 4

Figure 5:
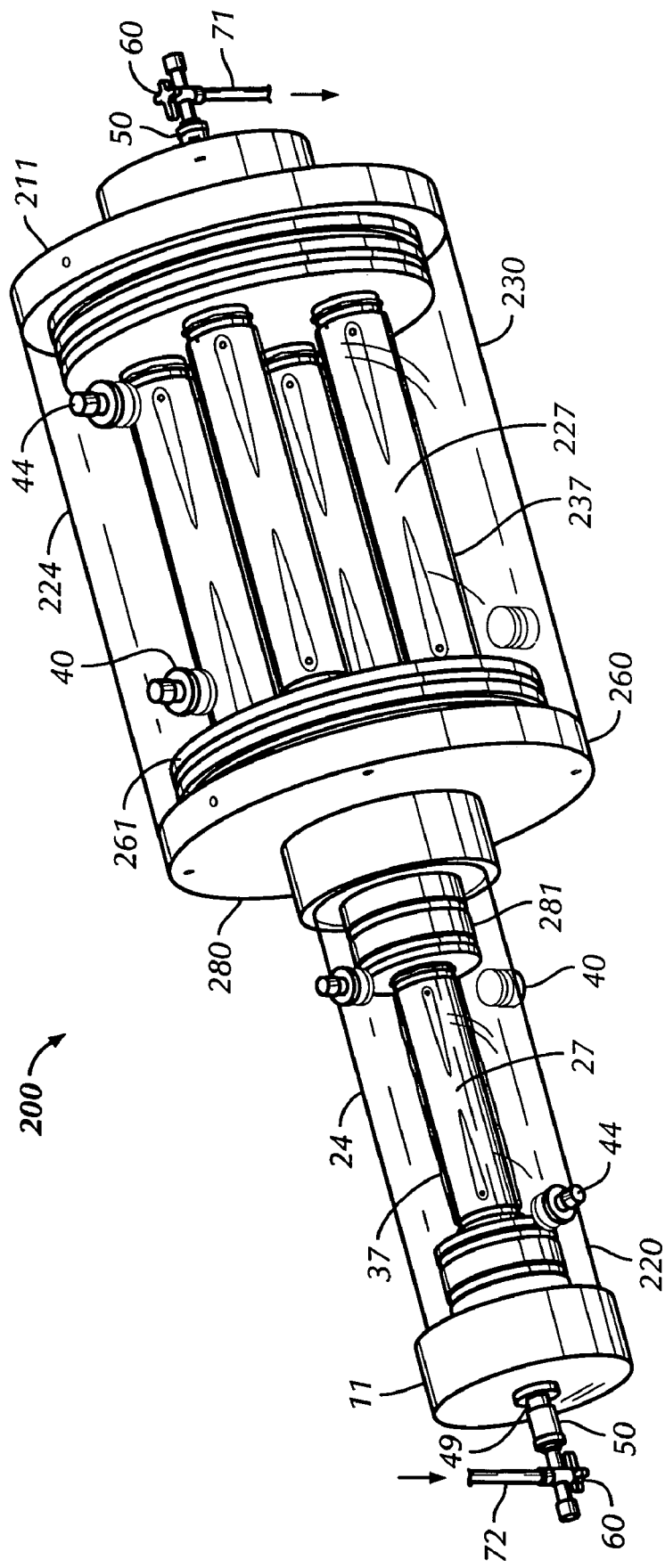
FIG. 5 shows an oblique view of interconnected culture chambers where the chambers have different capacities and the larger chamber has multiple diffusion membranes positioned within its interior.
Figure 6:
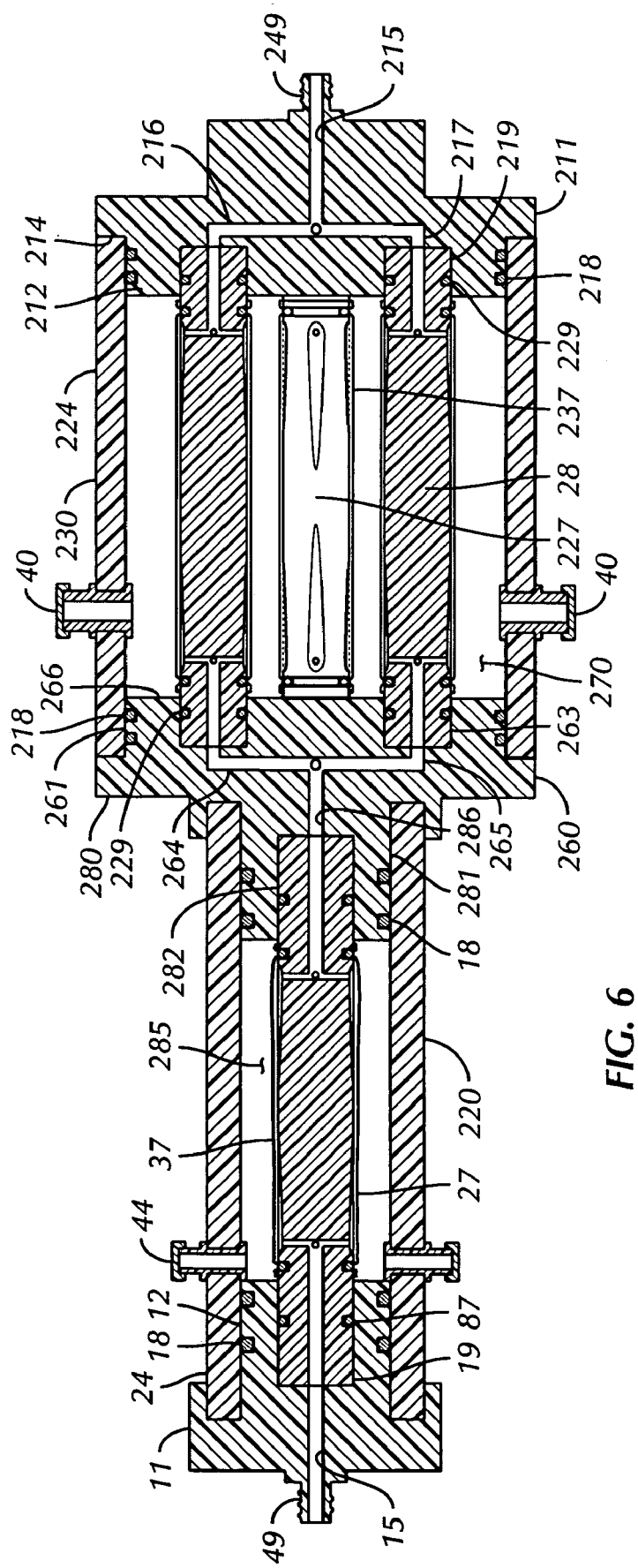
FIG. 6 is a longitudinal cross-sectional view of the interconnected culture chambers shown in FIG. 5.

Alternative Embodiment of Interconnected Culture Chambers of Different Capacities The bioreactor system 200 has interconnected culture chambers arranged as shown in both FIGS. 5 and 6. This arrangement basically utilizes two rigid coaxial culture chambers 220 and 230 cojoined in tandem, and utilizes bioreactor vessel types substantially similar to those disclosed in U.S. patent application entitled "Culture Chamber for Biologicals", Ser. No. 10/725,607.

The first chamber 220 utilizes a first molecular cutoff membrane 37 and is upstream of the second chamber 230. One of the features of this embodiment is the very large size of second chamber 230 relative to first chamber 220. The second chamber 230 is designed to provide more molecular cutoff membrane active surface area than is present in the first chamber 220. This arrangement is utilized when the first bioreactor chamber 220 is able to provide sufficient secretions to stimulate and/or nurture the cells in a larger second chamber 230.

The cojoined bioreactor chambers 220 and 230 are rotated as an unit using standard rotational equipment known to those in the industry, but with three supporting drive rollers which act on the tires of the end pieces 11 and 211 and the center hub 280.

The first chamber 220 produces a desired growth factor or mediator for supply to the second chamber 230. The bioreactor of the second chamber 230 uses a second molecular cutoff membrane 237 that is optimized for the cells and the outputs desired from the second chamber 230.

The first bioreactor chamber 220 of the bioreactor system 200 has all of its components including the input fluid system in common with that of the first chamber 20 of the bioreactor system 10 of the present invention, except that a different fluid connector or center hub 280 is used. Thus, first chamber 220 has an end piece 11 sealingly engaged on the inlet end of a sleeve 24 and also has a membrane carrier assembly 27 located axially within the interior of sleeve 24, thereby forming a bioreactor chamber as before. Multiple radial wall penetration ports 25 are provided in the annular wall of sleeve 24 to allow the introduction of one or more fill ports 40 and one or more samplingports 44.

The biologicals being cultured in the rotatable chambers 220 and 230 require nutrients, so fluid-conducting swivels 50, stopcock valves 60, fluid inlet tubing 72, and outlet tubing 71 are provided for the system. The system 200 is plumbed similarly to that of serially arranged bioreactor system 300 so that nutrient fluid enters the first chamber 220 of the system through inlet tubing 72, stopcock 60, and swivel 50. The fluid output from chamber 220 passes through hole 286 in center hub 280 into the second bioreactor chamber 230. The outflow from the second chamber 230 passes through a swivel 50, stopcock 60, and outlet tubing 71.

The growth compartment 285 of the first chamber 220 is located between the interior bore of the sleeve 24, the membrane carrier assembly 27, the interior end of interior projection 12 of end piece 11, and the interior end of the interior projection 281 of the center hub piece 280.

Center hub 280 is a structure composed of right circular cylindrical segments. The first side of the center hub 280 facing the first chamber 220 is basically the same about its transverse midplane as the corresponding side of center hub 80 of the bioreactor system 10 and likewise identical to the end piece 11 of the first chamber 220 with hose barb attachment neck 49 removed.

The external cylindrical portion of hub 280 adjacent the interior projection 281 serves as a tire for the rotation of the entire bioreactor assembly 200. The first interior projection 281 of center hub 280 also carries two male O-ring grooves that hold O-rings 18. The O-rings 18 mounted in the grooves of projection 281 of center hub 280 sealingly mate with and restrain the axial position of cylindrical sleeve 24. On its first side center hub 280 has a flat-bottomed cylindrical bore 282 for housing the membrane carrier assembly 27 of the first chamber.

The second side of the center hub 280, obverse to the first side of center hub 280, has in order from the transverse midplane of center hub 280 a cylindrical flange 260 and second interior projection 261. Flange 260 is the same diameter as or slightly larger than sleeve 224 used for the second chamber 230. Second interior projection 261 is sized to closely fit to the bore of sleeve 224 and has two male O-ring grooves mounting O-rings 218 to seal therewith.

An axial hole 286 provides communication from the counterbore 282 on the first side of the hub 280 to approximately the middle of hub 280. Axial through hole 286 penetrates through interior projection 281 and approximately midway into the body of center hub 280 and is there branched into a number of radial holes 264. Offset from the axis of center of hub 280 are parallel holes 265, each of which centrally intercepts a counterbored flat bottom hole 263 and a corresponding radial hole 264 in order to form a flow path for the fluid entering the second chamber 230. The multiple counterbored holes 263 are positioned in a regular pattern on the transverse face 266 of the reduced diameter end 261 of center hub 280. Optional lead-in chamfers are provided at the mouth of counterbores 263 in order to facilitate the stabbing of an O-ring seal 229 with the membrane carrier assembly 227. Thus hub 280 not only supports chambers 220 and 230 but also provides a flow connection between the chambers.

Sleeve 224 is similar in construction to that of sleeve 24 used with the first chamber 220, but differs only in its inner and outer diameters. The inner diameter of sleeve 224 is chosen to be sufficient to accommodate multiple membrane carrier assemblies 227 and provide sufficient volume for chamber 230. The outer diameter is selected for strength and rigidity. As is the case for sleeve 24, sleeve 224 has wall penetrations for the mounting of multiple fill ports 40 and samplingports 44. Sleeve 224 is a close fit to inner projection 261 of center hub 280.

End piece 211 has a right circular cylindrical central body having the same outer diameter as the enlarged flange 260 having a coaxial push-on hose barb attachment neck 249 on its outer face. Reduced diameter coaxial right circular cylindrical interior projection 212 extends inwardly on the transverse face of the interior end of end piece 211, with a transverse shoulder 214 located on the transverse interior face of end piece 211 immediately exterior of projection 212. The exterior cylindrical surface of interior projection 212 has annular male O-ring grooves. Elastomeric O-rings 218 are mounted in the O-ring grooves of projection 212.

Axial hole 215 penetrates through attachment neck 249 and approximately midway into the body of end piece 211 where it is branched into a number of radial holes 216. Offset from the axis of end piece 211 are parallel holes 217, each of which centrally intercepts a counterbored flat bottom hole 219 and a corresponding radial hole 216 in order to form a flow path for the fluid exiting from the second chamber 230. Optional lead-in chamfers are provided at the mouth of counterbores 219 in order to facilitate the stabbing of an O-ring seal 229 with the membrane carrier assembly 227. The pattern of counterbores 219 is the mirror image of the counterbores 263 in the center hub 280.

A membrane carrier assembly 27 as shown in FIGS. 5 and 6 for this bioreactor system 200 traverses the growth compartment 285. The membrane carrier 27 is identical to the unit used in the bioreactor systems 10 and 100 of the present invention. An end of the generally cylindrical membrane carrier assembly 27 is mounted in the counterbores 19 and 282 of each of the two assemblies 11 and 281, respectively, forming the end of compartment 285 used in chamber 220.

A membrane carrier assembly 227 as shown in FIGS. 5 and 6 traverses the growth compartment 270 of the second chamber 230. The membrane carrier 227 is substantially identical to the unit used in the first chamber 285, but it mounts the same or a different molecular cutoff membrane 237 that is optimized for the cell growth and collection of the end product in the second chamber 230. An end of the generally cylindrical membrane carrier assembly 227 is mounted in the counterbores 219 and 263 of each of the two assemblies 211 and 280, respectively, forming the end of compartment 270 used in chamber 230.

EXAMPLE 5

Interlinked Reusable Culture Chamber with Cell Filter

Example 2 illustrated the interlinking of two reusable bioreactors, each of which was traversed by a membrane carrier assembly 27. This Example shows the interlinking of two reusable bioreactors, where one of the bioreactors is not traversed by a membrane carrier 27 but has a filter to prevent the cells from flowing out of the bioreactor, while the media containing the cellular products does flow out of the bioreactor.

Referring to FIG. 7, the first bioreactor chamber 720 is located on the inlet side and serves to feed the second bioreactor chamber 730. Alternatively, the order of the bioreactor chambers 720 and 730 could be reversed so that the culture chamber 730 would be located on the inlet side to feed the second bioreactor chamber 720.

The bioreactor chamber 720 has an end piece 711 that seals to the upstream end of a right circular cylindrical tubular sleeve 724, while the center hub 780 seals to the downstream end of the sleeve 24 so that a growth compartment 795 is formed within the enclosed space. Multiple radial wall penetration ports 25 are provided in the annular wall of sleeve 724 to allow the introduction of one or more fill ports 40 and one or more samplingports 44.

When in use for culturing cells, cellular aggregates, particles, tissues and organoids, the culture chamber is designed to be supported on and rotated by a roller drive that rotates the chamber about its axis as described for the interconnected culture chambers 10.

End piece 711 has a right circular cylindrical central body having a coaxial push-on hose barb attachment neck 749 on its outer face. Axial through hole 715 penetrates through the attachment neck 749 and the rest of the body of end piece 711. Reduced diameter coaxial right circular cylindrical interior projection 712 extends inwardly on the transverse face of the interior end of end piece 711, with a flat-bottomed trepanned groove 714 located on the transverse interior face of end piece 711 immediately exterior of projection 712.

The exterior cylindrical surface of interior projection 712 has an annular male O-ring groove. Elastomeric O-ring 718 is mounted in the O-ring groove of the projection 712. Although not shown in FIG. 8, the right circular cylindrical sleeve 724 is preferably provided with a lead-in taper on each of its interior corners. The tapers facilitate the stabbing of O-ring 718 over the interior projections 712 and the stabbing of O-rings 723 over the interior projection 781 forming the ends of first chamber 720.

At each end of chamber 720, sleeve 724 is stabbed over the interior projections 712 and 781 and bottomed out in the trepanned grooves 714 and 782 at the interior ends of end piece 711 and the fluid connector or center hub 780, respectively. The interior bore of sleeve 724 is a close sliding fit to the outer diameter of interior projection 712 of end fitting 711, thereby permitting O-ring 718 to sealingly engage the bore of sleeve 724. O-ring 718 also serves to retain sleeve 724 in its desired axial position by virtue to its forceful frictional engagement with sleeve 724.

Center hub 780 is a structure composed of cylindrical components. The first side of center hub 780 has the interior projection 781 projecting toward the chamber 720. The second side of center hub 780 has the interior projection 721 projecting toward the chamber 730. An axial through hole 786 provides communication from one side of the hub to the other side, so that center hub 780 not only supports chambers 720 and 730, but also provides a flow connection between the chambers 720 and 730.

Reduced diameter coaxial right circular cylindrical interior projection 781 has a flat-bottomed trepanned groove 782 located on the transverse interior face of the center hub 780 immediately exterior of projection 781 into which the sleeve 724 fits. The exterior surface of the projection 781 carries two male O-ring grooves that hold O-rings 723. The O-rings 723 mounted in the O-ring grooves of center hub 780 sealingly mate with and restrain the axial position of cylindrical sleeve 724.

The projection 781 has a coaxial flat-bottomed counterbore 755 in its interior transverse end. A controlled porosity cell filter 750, which has a thickness less than the depth of the counterbore 755, is inserted into a flat-bottomed counterbore 755 to be externally flush with the top of the counterbore 755 thereby creating a collector plenum 757 between the filter 750 and the counterbore 755. The filter 750 allows the flow of media and nutrients from one chamber to the other chamber, but it prohibits cells or particles from leaving the chamber in which they are being cultured.

Reduced diameter coaxial right circular cylindrical projection 721 is substantially similar to the interior projection 82 of hub 80. The projection 721 has a flat-bottomed trepanned groove 783 located on the transverse interior face of the center hub 780 immediately exterior of projection 721 into which the sleeve 24 fits. The exterior surface of the projection 721 carries two male O-ring grooves that hold O-rings 18. The O-rings 18 mounted in the O-ring grooves of center hub 780 sealingly mate with and restrain the axial position of cylindrical sleeve 24.

A membrane carrier assembly 27, described above, traverses the bioreactor chamber 730 and its growth compartment 785. The interior end of the membrane carrier assembly 27 is mounted in the counterbore 762 of the projection 721. The other end of the membrane carrier assembly 27 is mounted in the counterbore of the end piece 11 that forms the outside end of the bioreactor chamber 730.

EXAMPLE 6

Interlinked Reusable and Disposable Culture Chambers

Figure 9:
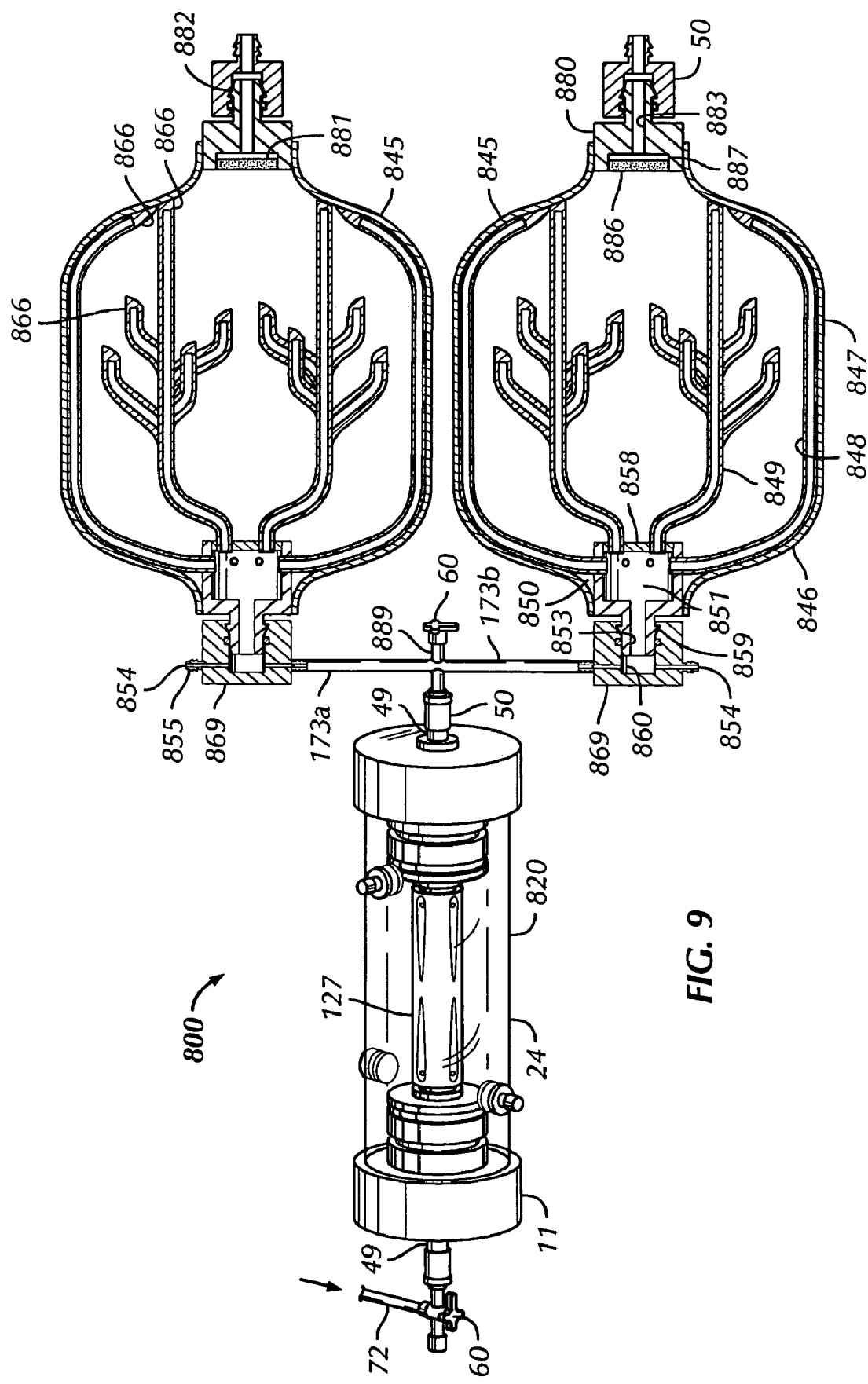
FIG. 9 is one embodiment of interconnected culture chambers with an oblique view of the first chamber shown and a longitudinal cross-sectional view of the other chambers shown.

Example 1 illustrated the interlinking of multiple reusable culture chambers. This Example shows one alternative configuration of interlinked reusable and disposable culture chambers. The bioreactor system 800 has serially arranged biological culture chambers as shown in FIG. 9. The arrangement of the system uses a single, separate rigid first chamber 820 with its outflow stream split and delivered to two independent, separate disposable bag second chambers 845. The second chambers 845 have provision for secondary nutrient streams to be added to the outflow stream from the first chamber.

Referring to FIG. 9, first chamber 820 has an essentially identical construction with that of chamber 120 of the bioreactor system 100 of the present invention. The first chamber 820 utilizes a first molecular cut-off membrane 137 and is upstream of the two culture chambers 845 of the second chamber set. The individual second chambers 845 are soft-sided disposable culture bags described in U.S. Pat. No. 6,673,598 and incorporated herein by reference.

FIG. 9 does not show the split cylindrical bag housing needed to support the culture bags 845 in order to see the culture chambers 845 more clearly. However, similar versions of this hardware are described below and in U.S. Pat. No. 6,673,598. Each of the bioreactor chambers 120 and 845 is rotated. The arrangement of the rotational equipment can be multiple independent sets of the standard rotators known to those in the industry, or alternatively a gang rotation system could be used. However, typically the bioreactor chambers 845 will be rotated identically so that a similar, balanced performance can be expected from the biological reactions within each chamber.

The first chamber 820 produces a desired growth factor or mediator for supply to the second set of chambers 845. The two bioreactors of the second chamber set may vary in configuration depending upon the desired used. The second chamber set, illustrated in FIG. 9, are identical to each other and use a molecular cutoff filter 886 optimized for the cells and the collection of end product from the second chamber set.

The bioreactor of the first chamber 820 has an end piece 11 sealingly engaged on each end of a sleeve 24 and also has a membrane carrier assembly 127 located axially within the interior of sleeve 24, thereby forming a bioreactor chamber as before. Multiple radial wall penetration ports 25 are provided in the annular wall of sleeve 24 to allow the introduction of one or more fill ports 40 and one or more samplingports 44.

The biologicals being cultured in the rotatable chambers 820 and 845 require nutrients, so fluid-conducting swivels 50 and 869, stopcock valves 60, intermediate tubing 173a,b, and fluid inlet tubing 172 are provided for the system. The system 800 is plumbed so that nutrient fluid enters the first chamber 820 of the system through inlet tubing 172, stopcock 60, and swivel 50. The fluid output from chamber 820 emerges through attachment neck 49 and swivel 50 of the outlet side endpiece 11 of the first chamber 820. The flow then passes to a fluid conducting cross fitting 889 which has connections to both the two second culture chambers 845 via identical intermediate tubing 173a,b and which also connects to another stopcock 60. The intermediate tubings 173a,b are generally identical in order to ensure the balanced flow of nutrients to the second chambers 845. The stopcock 60 on the cross fitting 889 can be used to control the flow of the fluid mixture delivered to the second chambers 845. The outflow from each of the second chambers passes through a swivel, a stopcock (not shown), and outlet tubings (not shown). This arrangement permits full control of the fluid system for the bioreactor system 800.

The second bioreactor chambers 845 utilize disposable flexible bags, in this instance bag assemblies 846. During fabrication of the bag assemblies 846, the end of a bag 847 will be sealingly welded or fused to the external cylindrical surfaces of the inlet 850 and outlet 880 bag ends.

To assist in mixing the fluid in the bag assembly 846, one or more optional perfusion tubes will be incorporated into the bag assembly. Two types of perfusion tubes, wall tubes 848 and internal tubes 849, are used for the purpose of introducing nutrients into the interior volumes of the second set of culture chambers 845. In the cross-sectional view of FIG. 9, the wall perfusion tubes 848 are mounted on the interior of each bag wall. Each wall perfusion tube 848 is supported over its length, beginning a small distance from the inlet plenum 851 of inlet bag end 850, by being joined integrally with a lapped bag seam. The perfusion tube 848 is symmetrically positioned in the seam and fused to the wall of bag 847 by welds on each side of seam. The weld joints only cover a portion of the circumference of the wall perfusion tubes 848, so that a substantial portion of each tube is still exposed to the interior volume of the bag 847.

Figure 10:
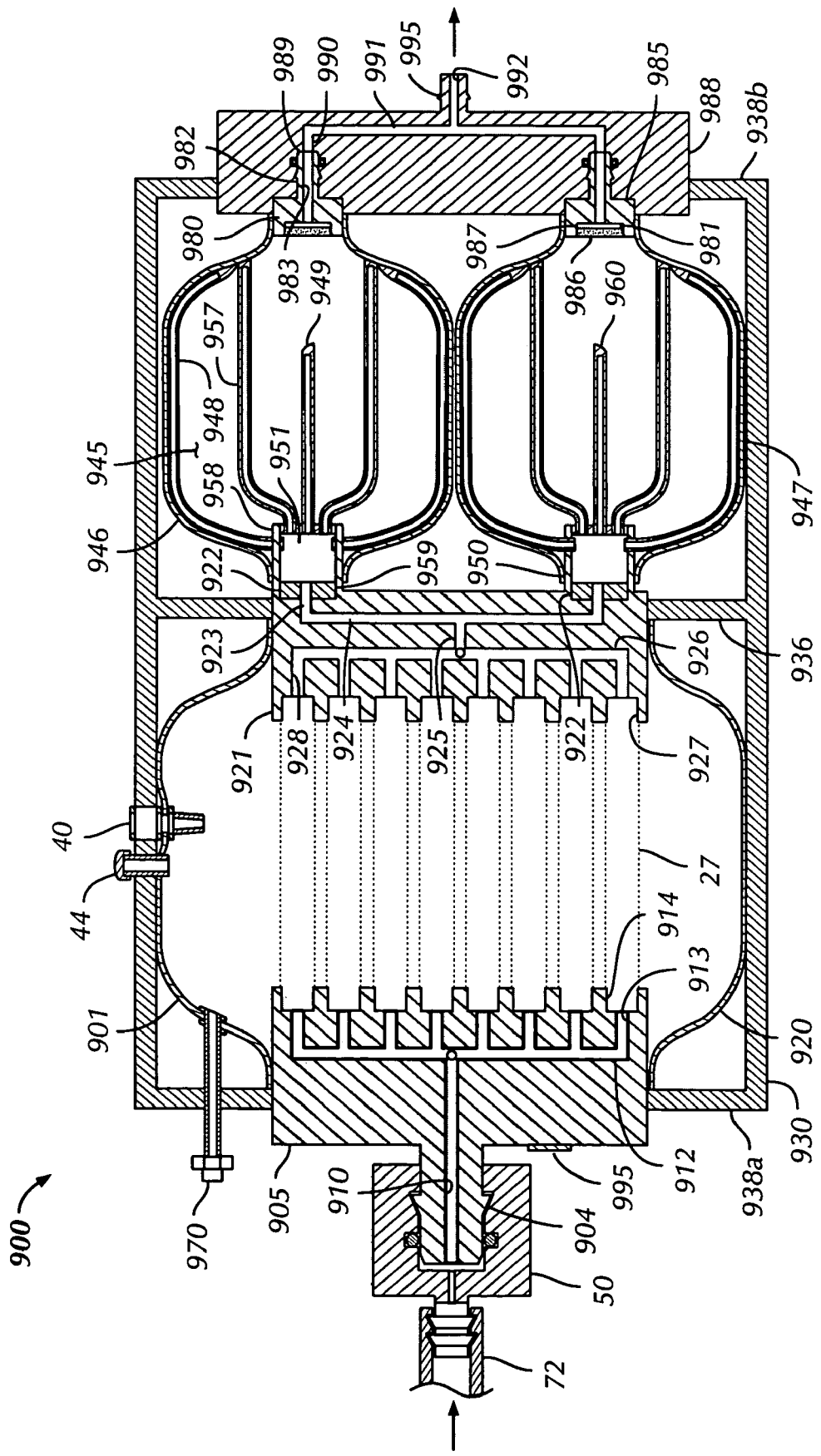
FIG. 10 is a longitudinal cross-sectional of a tandem bioreactor system wherein flexible disposable bioreactor chambers are mounted in tandem within a clamshell housing.
Figure 12:
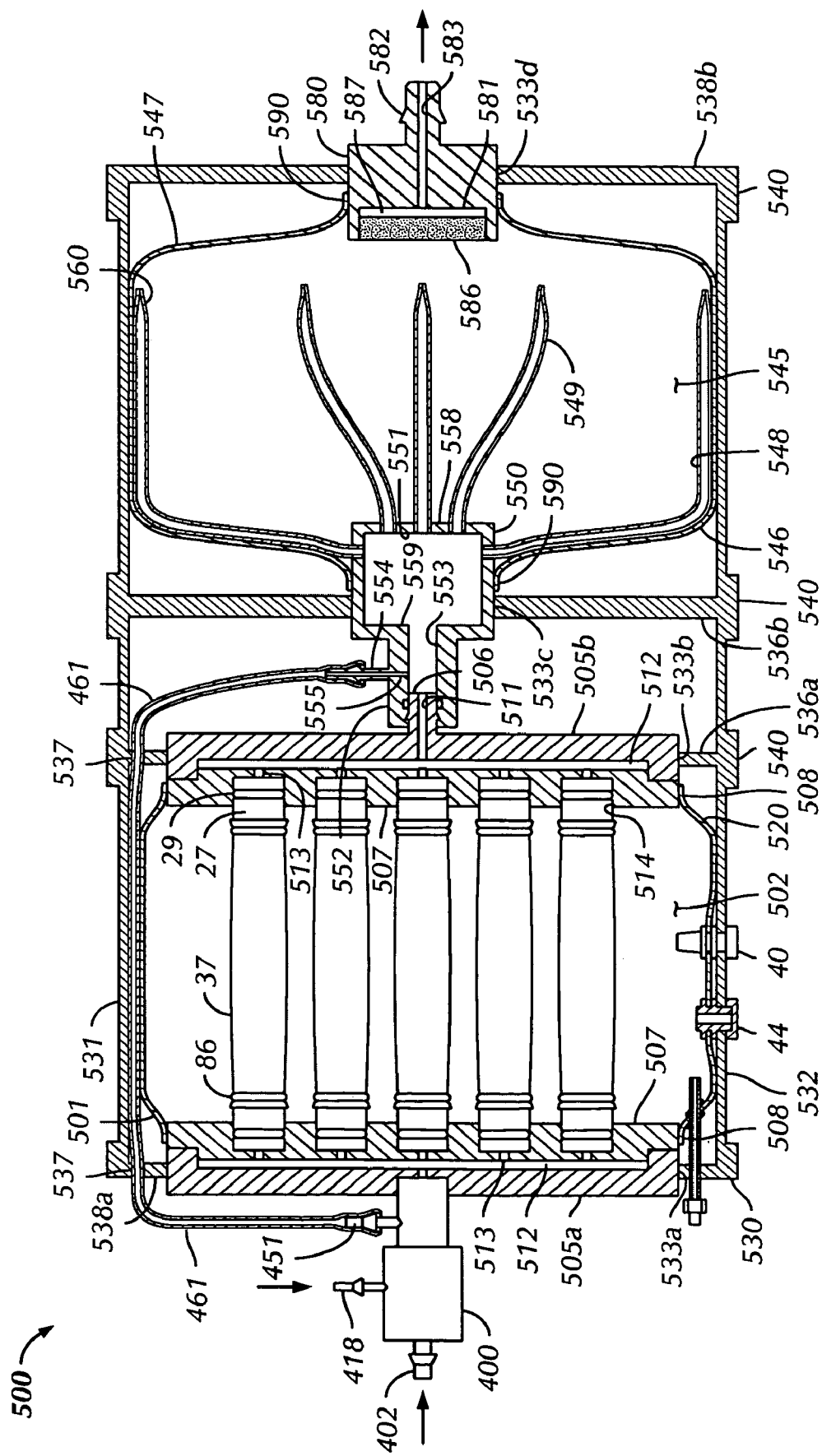
FIG. 12 is a longitudinal cross-sectional of another tandem bioreactor system wherein flexible disposable bioreactor chambers are mounted in tandem within a clamshell housing.

The bag assembly 846 may also have one or more end supported internal perfusion tubes 849 of various configurations. Example configurations are shown in FIGS. 9, 10 and 12. The internal tubes 849, shown in FIG. 9, extend from the inlet transverse end cap 858 into the interior of the bag assembly 846. The internal perfusion tubes 848 and 849 will vary in length, weight and flexibility, depending on the viscosity of the media. The internal perfusion tubes 848 and 849 move with the rotation of the bag support assembly 846, thus adding to the mixing of the media within the bag. Additionally, end supported tubes 849 (two shown) extend from the inlet plenum 851 to the other side of the bag 847, where they are anchored at their tips by welding to the inside of the bag. The end supported internal tubes 849 are branched to further aid perfusion and mixing within the bag assembly 846.

Each perfusion tube 848 and 849 has a distal closure 866 where the perfusion tube is closed or sealed by crimping and/or fusing. In contrast, the inlet end of each perfusion tube 848 and 849 is in communication with the fluid inlet plenum 851 for the bag assembly 846. The material of construction of perfusion tubes 848 and 849 is a biologically-compatible, non-toxic, non-protein-absorbing, flexible polymer having a number of perforations or a controlled permeability for the nutrient fluids for the biological media of the second chamber assembly 845, allowing fresh media to be pumped into each bag assembly 846 under a low pressure gradient, similar to a soaker hose used in watering lawns.

The exterior of the body of each inlet bag end 850 is a relatively thin walled right circular cylinder that is sized to have a close fit within the bag holder of its rotating assembly (not shown). On the interior end of inlet bag end 850 is located thin transverse inlet end cap 858. On the exterior end of inlet bag end 850 and adjoined to it by a transverse shoulder is reduced diameter cylindrical extension connecting neck 859, which has a coaxial through hole 853 penetrating into plenum 851. The exterior of connecting neck 859 has, in order from its attachment to bag inlet end 850, a first cylindrical section, an annular triangular cross-section latching detent with a transverse shoulder on its inner side, and a second cylindrical section having the same diameter as the first and mateable with a female O-ring. Inlet end cap 858, the outer transverse end of cylindrical inlet bag end 850, and the interior of the cylinder of inlet bag end 850 form inlet plenum 851.

The outflow stream from first chamber 820 freely passes by way of an outlet swivel 50 to cross fitting 889, branching there to intermediate tubings 173a,b and thence via dual input swivels 869 to the inlet plenums 851 for distribution into the interior of bag assemblies 846 through the perfusion tubes 848 and 849.

Multiple radial branch ports extend through the cylindrical wall of inlet bag end 850 and intersect inlet plenum 851. An attached outer perfusion tube 848 is fused into each branch port so that the bore of each tube 848 is in communication with inlet plenum 851.

Likewise, multiple interior perfusion tubes 849 are fused into corresponding branch ports that are provided in inlet end cap 858 coplanar with and at an angle ranging from 0° to 45° to the axis of the inlet end cap. Each end supported interior perfusion tube 849 thus has its bore in communication with inlet plenum 851.

Outlet bag end 880 is a right circular cylinder that has a coaxial flat bottom counterbore 881 in its interior transverse end and a connecting neck 882 for insertion into a receiving socket of a swivel 50. Concentric through bore 883 passes through neck 882 and intersects counterbore 881.

A controlled porosity cylindrical filter disk 886, which has a thickness less than the depth of counterbore 881, is sealingly mounted externally flush in counterbore 881, thereby creating collector plenum 887 between the filter disk 886 and the counterbore 881. Outflow fluid emerging from the second chamber 845 is filtered by disk 886 to prevent the cells within the second chamber from leaving that chamber, while at the same time waste products and the desired output products produced within second chamber 845 are passed by filter disk 886. A fluid swivel 50 is then attached to the connecting neck 882 of bag end 880 to convey the outflow from the second chamber system 845 to storage or processing.

The dual input swivel 869 serves both to commingle the outflow from the first bioreactor 820 with a separately supplied secondary nutrient stream and to convey that fluid through a rotating connection with the connection neck 859. The body of swivel 869 is cylindrical with transverse ends and a coaxial bore 860 that provides a close fit to the cylindrical portion of connection neck 859. From its interior end, the bore 860 has a female O-ring groove housing an O-ring that sealingly mates with the rotatable connection neck 859 of the bag assembly 846 and then a triangular cross-section annular groove with a transverse outer end. When the input swivel 869 is stabbed onto the connection neck 859, the annular ridge of the connection neck engages into the groove in the bore 860 so that the two parts are retained together. Dual input swivel 869 has two identical hose connection barbs 854 which are diametrically opposed on the outer cylindrical surface of the swivel body.

Coaxial through holes 855 pass through the barbs 854 and penetrate into the bore 860 of the swivel 869. For each of the two swivels 869, one barb 854 is attached to an intermediate tubing 173a or 173b, while the other is optionally attached to the tubing (not shown) that supplies the secondary nutrient stream to the swivel. If the other barb 854 is not attached to a secondary nutrient stream it is capped.

Interconnected Disposable Bioreactor Bags

Disposable culture bags, or bioreactor bags, are needed by the biotechnology industry to cut down on the time and expense of cleaning, sterilizing and verifying bioreactors with each new batch of product.

The present invention includes a reusable bag housing to support interconnected disposable culture chambers such as the bioreactor system 900 shown in FIG. 10. Since the bag assemblies are designed to be supported by a bag support housing, very large capacity bag assemblies can be used to scale-up production procedures. The bag assemblies described herein are made to hold anywhere from milliliters to thousands of liters of fluid. Furthermore, the bag assemblies described herein are pre-sterilized before use, typically done using gamma radiation or gas.

The bioreactor bags are housed in a rotatable housing and rotated by a drive mechanism as described in pending U.S. Pat. No. 6,673,598 B1. The disposable bioreactor bags have rigid end pieces that can be configure to carry one or more membrane carrier assemblies 27 with molecular weight cut-off membranes 37.

EXAMPLE 7

Interconnected Disposable Culture Chambers

The bioreactor system 900 has serially arranged biological culture chambers as shown in FIG. 10. This arrangement of the system uses a disposable flexible bag assembly 901 for the first chamber. However, multiple disposable bag assemblies 946 mounted in parallel are used for the second chamber system. The bags used for the second chamber system are constructed with multiple diffusion tubes and an outlet filter. All of the bags are mounted in a single cylindrical bag support housing 930 for rotation as a unit. This particular arrangement is desirable when the interior volumes of the second chamber bags 946 must be kept relatively small.

The arrangement shown in FIG. 10 is also desirable when different types of end products are desired from different cells being simultaneously grown in the system. In this latter case, the outputs of the second chamber system would not be commingled as shown in FIG. 10, but would flow through a dual conduit hydraulic swivel 400, shown in FIG. 11, coaxially mounted on bag support housing 930 so that the outputs of the second chamber bags would be maintained separately.

Alternatively arrangement of the bioreactors shown in FIG. 10 may be switched so that there are multiple chambers 946 on the first side and the chamber 901 on the second side. This arrangement would be advantageous if a cell line required growth factors or products produced by more than one cell type.

The type of chambers (with or without membrane carrier assemblies, perfusion tubes, or both) used in the bioreactor system can be varied as desired. Furthermore, varying the width or the length of the chambers can vary the size of the chambers. The housing 930 is configured to support and rotate the bioreactor system designed by the investigator to meet specific growth requirements.

Referring to FIG. 10, bag assembly 901 is constructed to support, by means of mounting in bag ends 905 and 921, multiple membrane carrier assemblies 27 within the interior of the bag 920. The bag assembly 901 includes bag 920, two end pieces 905 and 921 for establishing fluid interconnections and positioning the bag assembly 901, and the multiple membrane carrier assemblies 27.

Bag assembly 901 includes multiple service ports such as a gas venting port 44 and a fill port 40. The fill port 40 is bonded into a penetration in the side of bag 920, and the samplingport 44 also is bonded into a penetration in the side of bag 920. The attachments of ports 44 and 40 into bag 920 are reinforced by sealing grommets on both sides of the bag wall, as is well understood by those skilled in the art. Additionally, a quick fill port 970 is inserted into a reinforced hole in the wall of bag assembly 901 and welded in so that it has a position parallel to and offset from the axis of bag assembly 901. The bag assembly 901 has its constituent components welded or bonded or fused together. Furthermore, all of the components of the bag assembly 901 contacting the biological media are biologically non-reactive, non-toxic and exhibit low protein binding properties.

Bag inlet end 905 is a right circular cylindrical disk having a concentric connecting neck 904 on its outer transverse face. Connecting neck 904 has, in sequential order from the outer face of bag end 905, a straight cylindrical shank, an externally projecting frustro-conical latching shoulder, and a second straight cylindrical outer shank, so that it can be latched into swivel 50. Coaxial hole 910 is located on the axis of connecting neck 904 and penetrates through the length of connecting neck 904 and part way into the main cylindrical body of bag end 905. Hole 910 is intersected by multiple equispaced radial cross holes 912 which extend from the central axis of bag inlet end 905 approximately 90 percent of the distance to the outer cylindrical face.

The interior transverse end of bag interior end 905 has multiple angularly equispaced flat-bottomed counterbores 914 located in multiple concentric ring patterns. Each counterbore 914 is intercepted by the short coaxial blind holes 913, which are in turn intersected by the radial cross holes 912. Accordingly, a fluid path is created from the hole 910 transversing connecting neck 904, through the cross holes 912 and the short connecting holes 913 into each of the counterbores 914. The diameter of counterbore 914 is such that it provides a close fit to the outer diameter of the inlet end of the membrane carrier assembly 27.

Bag outlet end 921 is structured very similarly to bag inlet end 905 in general and is basically identical to its interior end. The bag outlet end 921 is a right circular cylindrical disk having multiple flat bottom counterbored sockets 922 on its outer transverse face in a single concentric regular circular array. Each of the sockets 922 has a short coaxial connecting hole 923 which is intercepted by a radial hole segment 924 which extends from its hole 923 to the center axis of bag outlet end 921, where it intersects short axially positioned central hole 925. Coaxial hole 925 is intersected by multiple equispaced radial cross holes 926 which extend from the central axis of bag outlet end 921 approximately 90 percent of the distance to the outer cylindrical face.

The interior transverse end of bag outlet end 921 has multiple angularly equispaced flat-bottomed counterbores 927 located in multiple concentric ring patterns identical to those in bag inlet end 905. Likewise, the pattern of radial holes 926 is identical to that of radial holes 912 of bag inlet end 905. Each counterbore 927 is intercepted by the short coaxial blind holes 928, which are in turn intersected by the radial cross holes 926. Accordingly, a fluid path is created from the counterbores 927, holes 928, through the radial cross holes 926 and the short connecting holes 925 and 923 into each of the counterbored sockets 922.

The diameter of the counterbores 922 is such that they provide a close fit to the outer diameter of the exit end of the support cylinder of the membrane carrier assembly 27. At bag assembly, the bag inlet end 905 and the bag outlet end 921 have their respective counterbores 914 and 927 aligned and the membrane carrier assemblies 27 are all sealingly inserted and bottomed in their socketing counterbores 914 and 927. The bag ends 905 and 921 are then circumferentially welded or otherwise fused on their outer cylindrical faces to the corresponding ends of bag 920 at the end openings. The length of the bag assembly is chosen to accommodate the membrane carrier assemblies used.

The membrane carrier assembly 27 transversing the bag assembly 900 has been previously described and is shown in detail in FIGS. 2 and 3. The first O-rings 87 provide a seal between the counterbores 914 and 927 and the carrier assembly 27. The membrane 37 is retained in place over the outer diameter of the central portion of support cylinder 28 by the use of second O-rings 87 to seal and anchor each end of membrane 37 into each groove 31.

The second bioreactor chamber utilizes multiple disposable flexible bags, in this instance multiple bag assemblies 946, mounted within the support housing 930 between its outlet end bulkhead 938b and its internal diaphragm 936. Each of the bag ends 950 and 980 are respectively supported by the counterbored sockets 922 on the outlet transverse side of outlet bag end 921 and in the counterbored sockets 985 of the bag header 988, respectively. During fabrication of the second bag assemblies 946, the ends of bags 947 will be sealingly fused or welded to the external cylindrical surfaces of the inlet 950 and outlet 980 bag ends.

To assist in mixing the fluid in the bag assembly 946, one or more optional perfusion tubes will be incorporated into the bag assembly. Three types of perfusion tubes 948, 949, and 957 are used for the purpose of inducing nutrients into the interior volumes of second bioreactor chamber system 945. In the cross-sectional view of FIG. 10, multiple outer perfusion tubes 948 are mounted on the interior of each bag wall. Each outer perfusion tube 948 is supported over its length, beginning a small distance from the inlet plenum 951 of inlet bag end 950, by being joined integrally with a lapped bag seam. The perfusion tube 948 is symmetrically positioned in the seam and fused to the wall of bag 947 by welds on each side of seam. The weld joints only cover a portion of the circumference of the outer perfusion tubes 948, so that a substantial portion of the tubes is still exposed to the interior volume of the bag 947.

The bag assembly 946 may also have one or more cantilevered internal perfusion tubes 949 of various configurations. As seen in FIG. 10, tubes 949 extend from the inlet transverse end cap 958 into the interior of the bag 947. The internal perfusion tubes 948 and 957 will vary in length, weight and flexibility, depending on the viscosity of the media. The internal perfusion tubes 948 and 957 move with the rotation of the bag support assembly 946, thus adding to the mixing of the media within the bag. Additionally, end supported tubes 957 (two shown) extend from the inlet plenum to the other side of the bag 947, where they are anchored at their tips by welding to the inside of the bag.

Each perfusion tube 948, 949, and 957 has a distal closure 960 where the perfusion tube is closed or sealed by crimping and/or fusing. In contrast, the inlet end of each perfusion tube 948, 949, and 957 is in communication with the fluid inlet plenum 951 for the bag assembly 946. The material of construction of perfusion tubes 948, 949, and 957 is a biologically-compatible, non-toxic, non-protein-absorbing, flexible polymer having a number of perforations or a controlled permeability for the nutrient fluids for the biological media of the second chamber assembly 945, allowing fresh media to be pumped into each bag assembly 946 under a low pressure gradient, similar to a soaker hose used in watering lawns.

The exterior of the body of each inlet bag end 950 is a relatively thin walled right circular cylinder that is sized to have a close slip fit within its comating flat bottom counterbored socket 922 of the outlet bag end 921 of the first bag assembly 901. On the interior end of inlet bag end 950 is located thin transverse inlet end cap 958. On the exterior end of inlet bag end 950 is reduced diameter cylindrical extension 959, which has a coaxial through hole 923 penetrating into plenum 951. The exterior of cylindrical extension 959 has a male O-ring groove with an O-ring to seal to the bore of socket 922 of the outlet bag end 921 of the first chamber 901. Inlet end cap 958, the inner end of cylindrical extension 959, and the interior of the cylinder of inlet bag end 950 form inlet plenum 951. The flow stream from the first chamber 901 freely passes to the inlet plenum 951 for distribution into the interior 945 of bag assembly 946 through the tubes 948, 949, and 957.

Multiple radial branch ports extend through the cylindrical wall of inlet bag end 950 and intersect inlet plenum 951. An attached outer perfusion tube 948 is fused into each branch port so that the bore of each tube 948 is in communication with inlet plenum 951. Likewise, multiple interior perfusion tubes 949 and 957 are fused into corresponding branch ports that are provided in inlet end cap 958 coplanar with and at an angle ranging from 0° to 45° to the axis of the inlet end cap 958. Each cantilevered interior perfusion tube 949 and 957 thus has its bore in communication with inlet plenum A 951.

Outlet bag end 980 is a right circular cylinder that has a coaxial flat bottom counterbore 981 in its interior transverse end and a connecting neck 982 for insertion into a receiving socket 989 of bag header 988. Concentric through bore 983 passes through neck 982 and intersects counterbore 981.

Controlled porosity cylindrical filter disk 986, which has a thickness less than the depth of counterbore 981, is sealingly mounted externally flush in counterbore 981, thereby creating collector plenum 987 between the filter disk 986 and the counterbore 981. Outflow fluid emerging from the interior of the second chamber 945 is filtered by disk 986 to prevent the cells within the second chamber from leaving that chamber, while at the same time waste products and the desired output products produced within the second chamber are passed by filter disk 986.

Bag header 988 is a thick circular disk that has an equispaced circular pattern of flat bottom counterbored sockets 985 located in its interior transverse face. The pattern for sockets 985 is the same as the pattern of sockets 922 in the outer face of outflow bag end 921 of the first bag assembly 901. A short hole 990 coaxial with each socket 985 penetrates approximately 60 percent of the way through bag header 988, where it intersects one of an array of radial holes 991 which extend from short hole 990 to the center axis of the bag header. Hole 992 extends outwardly along the axis of bag header 988 from the intersections of the radial holes 991 through outwardly extending coaxial connecting neck 995. Functionally, connecting neck 995 is substantially similar to connecting neck 904 of the first bag assembly 901, so it has an annular latching ridge to effect a latching with an outlet fluid swivel 50. A fluid swivel 50 (not shown) is then attached to the connecting neck 995 of bag header 988 to convey the outflow from the interior of the second chamber system 945 to storage or processing.

In addition the bag assemblies 901 and 946 are provided with a unique identifier 995. This identifier 995 may be a bar code, a magnetic strip or any other identifier to enable the user of the bioreactor system to easily track the bioreactor bags and the cells, cellular aggregates, particles, tissues or organoids and their end products through growth and processing.

Although the bag support housing 930 may be made any shape, the bag support housing is preferably a circular cylinder to ease its horizontal rotation. Bag support housing 930 is a circular cylinder having transverse end bulkheads 938a,b. The arrangement used for this embodiment 900 is similar to the unit 530 shown in FIG. 12 with the bioreactor system 500. Bag support housing assembly 930 (having certain features shown in more detail in FIGS. 3–5 of U.S. Pat. No. 6,673,598) is hollow so that its cylindrical wall has a uniform wall thickness.

Bag support housing 930 is provided with an internal diaphragm 936 that serves to support the outlet end of the first bioreactor chamber 901. Preferably bag support housing 930 has a diametrical split so that it is divided into a top portion and a bottom portion, where the top and bottom portions are hinged together on one cylindrical side of the diametrical split and a latch is provided on the opposed side of the diametrical split. The hinge allows the top portion and the bottom portion of the bag support assembly 930 to be selectably opened and closed.

Central concentric bores are located in both the transverse inlet and outlet bulkhead ends 938a,b and the central diaphragm 936 of the bag support assembly 930 and are designed to fit around the bag ends 905 and 921 and the bag header 988 of the second bioreactor bag assembly 946, while additional offset bores are located on the diametrical split so that they can readily accommodate insertion of fill ports into the split bore. One or more additional radial ports with clearance to permit insertion of a corresponding number of gas removal ports are appropriately positioned in the cylindrical walls of the upper and lower portions of the bag support housing 930. The drive assembly (not shown) rotates the bag support assembly 930 so that the axis of the bag support assembly and its contained bags is horizontal.

One advantage of bag support housing 930 is that the bag assemblies 901 and 946, which are made with their inlet and outlet connections incorporated into the bag assembly so that they can be coupled and also preplumbed to their respective inlet 72 and outlet 71 tubings, can be inserted into the bag support housing 930 without having to disconnect any tubing or connectors. A drive assembly (not shown) horizontally rotates the bag support assembly 930.

EXAMPLE 8

Interconnected Disposable Culture Chambers with Externally Added Media

Figure 11:
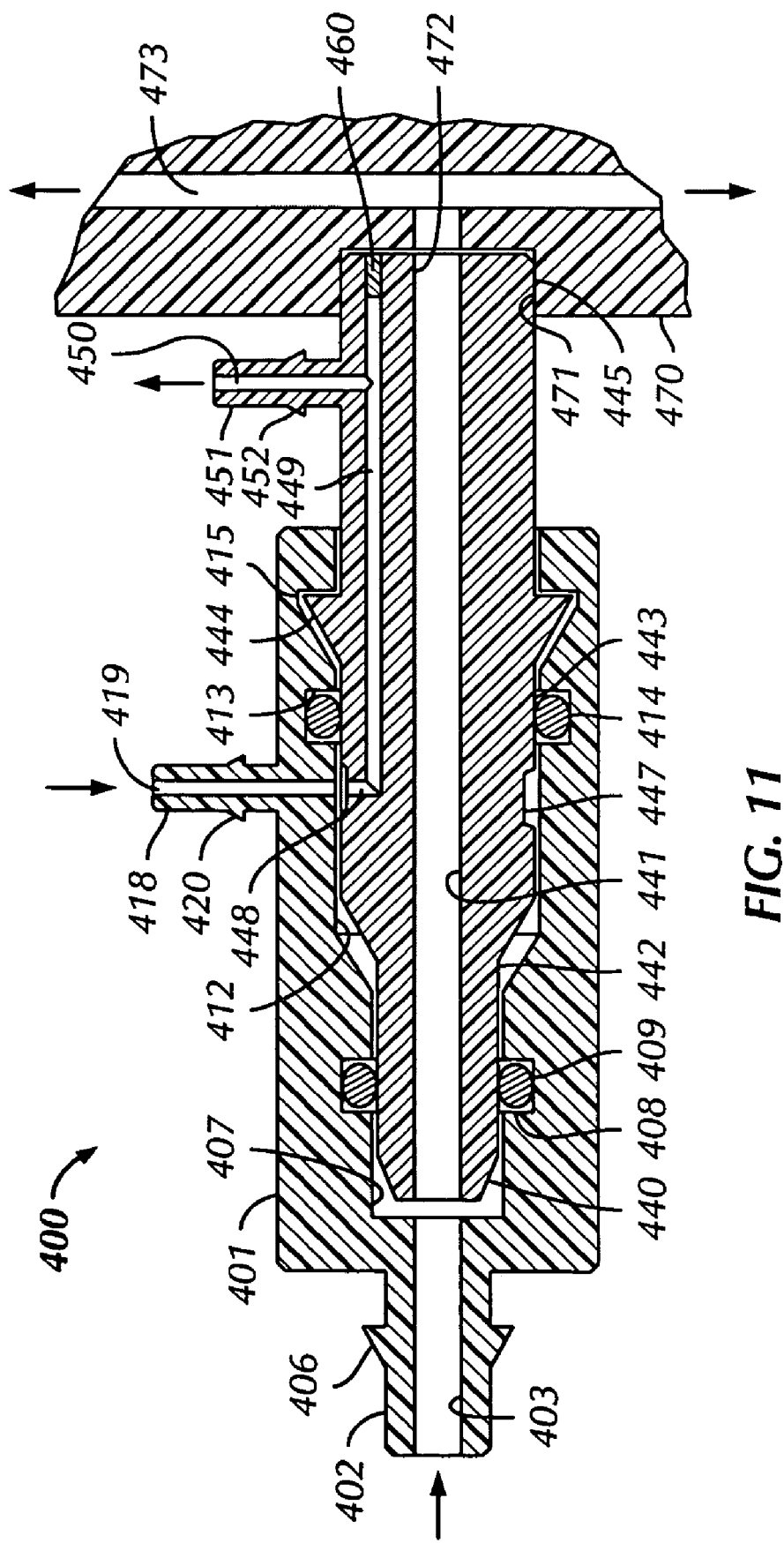
FIG. 11 is a longitudinal cross-sectional view of a dual conduit hydraulic flow swivel adapted for conveying two separate fluids into or out of a rotating bioreactor system.

Alternative bioreactor systems not only allow secretions from a first culture chamber to flow into a second culture chamber, but they also allow externally added media and nutrients to be added to the second culture chamber. In order to allow media to be added to the second culture chamber in controlled proportions with the culture secretions from the first chamber, a dual conduit hydraulic swivel 400 is used as shown in FIG. 11.

Swivel 400 consists of a cylindrical outer body 401 and a core piece 440. Outer body 401 has an axially projecting hose barb 402 on its first end, with axial first flow hole 403 extending through the barb and into first interior cylindrical cavity 407. Triangular cross-section external annular ridge 406 is located on barb 402 to sealingly and axially engage an attached hose.

First interior cylindrical cavity 407 has a centrally positioned female O-ring groove 408 mounting O-ring 409. Cavity 407, at the end opposed to the hose barb 402 side, has a conical transition where it intercepts a coaxial second interior cylindrical cavity 412. The second interior cylindrical cavity 412 has a female O-ring groove 413 mounting O-ring 414 and an annular latch groove 415 having right triangular cross-section wherein the transverse shoulder of groove 415 is on the exterior end of cavity 412. Furthermore, a radial hose barb 418 extends off of the outer body 401. A second axial through flow hole 419 penetrates through the hose barb 418 and into the second cavity 412 inside of the O-ring groove 413. The radial hose barb 418 has a triangular cross-section external annular ridge 420 to engage an attached hose.

The body of core piece 440 is basically a stepped cylinder with a central axial through hole 441 that serves as a coaxial extension of first flow hole 403. Core piece 440 is fully inserted into the bore of outer body 401. From its inner end which is inserted into the interior of outer body 401, the exterior of core piece 440 has a taper which permits stabbing into O-ring 409, a first cylindrical section 442 closely fitting to cavity 407, a conical transition shoulder which permits stabbing into O-ring 414, and a second cylindrical section 443 closely fitting to cavity 412. Core piece 440 has a coaxial annular triangular cross-section latching ridge 444 outward of O-ring groove 413 in a position where it can readily mate with and latch with latch groove 415 and thus hold the swivel 400 in proper axial alignment.

Radial port 448 intercepts shallow annular external groove 447 on cylindrical section 443 and both are located in the same transverse plane as second radial hose bard 418. Third flow hole 449 is parallel to and offset from axial hole 441 of core piece 440. Third flow hole 449 extends from the exterior end of core piece to intercept radial port 448. Third flow hole is plugged with insert plug 460 at its outer end. Radial hose barb 451 has an axial fourth flow hole 450 intercepting into third flow hole 449. O-rings 409 and 414 and plug insert 460 isolate a continuous flow path consisting of the radial port 440, the second 419, third 449, and fourth 450 flow holes and groove 447. Hose barb 451 has a triangular cross-section external annular ridge 452 to engage an attached hose.

The external end of core piece 440 of swivel 400 is mounted into mounting flat bottom counterbore 471 centrally positioned in a bioreactor bag end 470, where it is glued or welded at circumferential joint 445. Bioreactor bag end 470 has a short axial hole 472 communicating with counterbore 471 on its outer end and radial distributor holes 473 on its inner end.

A primary or first fluid path consisting of first flow hole 403 of outer body 401, axial hole 441 of core piece 440, and hole 472 of cell end piece 470 thus is created from hose barb 402 into the distributor holes 473 of cell end 470. An independent secondary fluid flow path consisting of the second flow hole 419 of outer body 401, the radial port 448, the third flow hole 449 and fourth flow hole 450 with groove 447 of core piece 440 is also provided. Thus the swivel 440 can handle a flow stream entering through the primary flow path, as well as the secondary flow path. This dual conductor hydraulic swivel arrangement 400 can thus be used not only to provide a primary nutrient stream to the upstream first chamber of a coaxially positioned and serially tandem mounted reactor system, but the secondary flow stream can be used to augment or otherwise modify the flow stream from the first chamber to the second chamber of the bioreactor system. Utilizing automated pumps, the flow of the primary and secondary fluid streams can be regulated and their flow proportioned as desired.

A bioreactor system 500 shown in FIG. 12 utilizes swivel 400 to simultaneously add outflow from the first culture chamber 501 and a second source of media with nutrients and other factors needed by the cells in the second culture chamber 546. The bag assembly 501 constituting the first chamber of the serially arranged culture chambers of the bioreactor system 500 includes bag 520 which has two similar end pieces 505a and 505b for establishing fluid interconnections and positioning the bag assembly 501.

The bag assembly 501 of the system 500 is configured to mount multiple membrane carrier assemblies 27 in an array symmetrical about the longitudinal axis of bag 520. Bag assembly 501 also includes multiple service ports such as a gas venting port 44 and a fill port 40. The fill port 40 is bonded into a penetration in the side of bag 520. The samplingport 44 is also bonded into a penetration in the side of bag 520. The attachments of ports 44 and 40 into bag 520 are reinforced by sealing grommets on both sides of the bag wall, as is well understood by those skilled in the art.

The bag assembly 501 has its constituent components welded or bonded or fused together. Furthermore, all of the components of the bag assembly 501 contacting the biological media are biologically non-reactive, non-toxic and exhibit low protein binding properties.

Preferably the bag 520 is made of a plurality of layers such as the multilayered fabric construction used in the synthesis of custom bags manufactured by Newport Biosystems, Inc. (Anderson, Calif.). Outlet side bag end 505b is a right circular cylindrical disk having a concentric connecting neck 506 on its outer transverse face. Connecting neck 506 has, in sequential order from the outer face of bag end 505b, a straight cylindrical shank, an externally projecting frustro-conical latching shoulder, and a second straight cylindrical outer shank. The inward end of the frustro-conical latching shoulder has a transverse shoulder, while the outward end has the same diameter as that of the second shank.

Coaxial hole 511 is located on the axis of connecting neck 506 and penetrates through the length of connecting neck 506 and part way into the main cylindrical body of bag end 505b. Hole 511 intersects short coaxial cylindrical cavity 512 that has a diameter of approximately 90 percent of the outer cylindrical face of bag end 505b. Flanged disk 507 has a thin outer flange which has the same outer diameter as bag end 505b and a main cylindrical body which is a close fit to the bore of cavity 512 and is bonded thereto, thereby closing cavity 512. The outer side of disk 507 that is exposed to the interior of bag assembly 501 has an array of multiple regularly spaced flat bottom counterbores 514. The array of counterbores 514 may be placed in a hexagonal pattern or in multiple hole circles and may include a counterbore on the axis of bag end 505b, as shown in FIG. 12.

Each counterbore 514 is intercepted by its short coaxial hole 513 that penetrates into cavity 512. Accordingly, a fluid path is created from the hole 511 traversing connecting neck 506, through the cavity 512 and the short connecting holes 513 into each of the counterbores 514. The diameter of each of the counterbores 514 is such that they provide a close fit to the outer diameter of their comated support cylinders 28 of the membrane carrier assemblies 27. Outlet bag end 505b is circumferentially welded or otherwise fused at 508 on its outer cylindrical face to the corresponding end of bag 520 at its end opening. Both the bag ends 505a,b are aligned so that their counterbores 514 are coaxial prior to attachment to the bag 520.

Bag end 505a is substantially identical to bag end 505b, except that instead of having a connecting neck 506, a short axially positioned flat bottom counterbore is provided in the outer end of bag end 505a and swivel 400 is bonded therein, as shown in FIG. 12. This counterbore intersects hole 511, so that an inlet flow path is thereby established.

The membrane carrier assembly 27 transversing the bag assembly 501 has been previously described and is shown in detail in FIG. 3. Each of the carrier assemblies 27 has its ends slipped into and bottomed in the comating counterbores 514 on the interior faces of the bag ends 505a,b. The O-rings 87 provide a seal between the counterbore 514 and the support cylinder 28 of the carrier assembly 27. The membrane 37 is retained in place over the outer diameter of the central portion of support cylinder 28 by the use of O-rings 87 to seal and anchor each end of membrane 37 into each groove 31.

Bag assembly 501 has inlet fluid coupling swivel joint 400, shown in detail in FIG. 11, to allow the bag assembly 501 to freely rotate along with its bag support housing 530 while connected to the primary input fluid feed tubing (not shown) which is attached to hose barb 402. Swivel joint 400 is also attached to a secondary fluid input stream supply tube (not shown) that is connected to hose barb 451 of the swivel. The core piece 440 of swivel 400 is axially mounted in a counterdrilled flat bottom hole on the exterior side of bag end 505a.

Although the bag support housing 530 may be made any shape, the bag support housing is preferably a circular cylinder having transverse end bulkheads 538a,b to ease its horizontal rotation. Bag support housing assembly 530, as described above for housing 930, has the external shape of a right circular cylinder and is hollow so that it has a uniform wall thickness. Bag support housing 530 is provided with two internal diaphragms 536a,b that serve to support the outlet and inlet ends of the first culture chamber 501 and second culture chamber 546 respectively. An axial gap is provided between the internal diaphragms 536a,b of bag support housing 530 for providing space for the interconnections between the first and second bioreactor chamber bags.

Bag support housing 530 has a diametrical split so that it is divided into a top portion 531 and a bottom portion 532, where the top and bottom portions are hinged together on one cylindrical side of the diametrical split and a latch is provided on the opposed side of the diametrical split. The hinge allows the top portion 531 and the bottom portion 532 of the bag support assembly 530 to be selectably opened and closed, although these features are not explicitly shown in FIG. 12.

Central concentric bores 533a,b,c,d are located in both the transverse inlet and outlet bulkhead ends 538a,b and central diaphragms 536a,b of the bag support assembly 530 and are designed to fit in the external annular grooves around the bag ends 505a,b and the bag ends 550 and 580 for the second bioreactor chamber bag 546, while additional offset bores are located on the diametrical split so that they can readily accommodate insertion of fill ports into the split bore. One or more additional radial ports with clearance to permit insertion of a corresponding number of gas removal ports are appropriately positioned in the cylindrical walls of the upper 531 and lower 532 portions of the bag support housing 530. Although gas removal ports and fill ports are not shown in the cross-sectional view of the second culture chamber 546 shown in FIG. 12, bag 547 has both fill ports and gas removal ports that must be accounted for when designing the bag support housing 530. The positioning of the radial ports need not be on the diametrical split of the bag support assembly 530.

A pair of coaxial holes 537 are located parallel to the axis of housing 530 and offset from the axis of the housing so that they are tangent to the inner wall of the housing. These holes 537 serve to accommodate secondary fluid delivery hose 461, which is attached to hose barb 451 and bypasses the first bioreactor chamber in bag assembly 501 so that the secondary fluid can be delivered to the second bioreactor chamber bag. Bag assembly 501 presses secondary fluid delivery hose 461 against the interior wall of housing 530 when the bag is filled, but the hose 461 is not collapsed. Additionally, annular external tires 540 having cylindrical outer surfaces are provided on the exterior of bag support housing 530 to facilitate driving the housing by means of an external rotational drive system (not shown).

One advantage of bag support housing 530 is that a bag assembly such as 501 made with an inlet and outlet system incorporated into the bag assembly 501 can be inserted into the bag support housing 530 without having to disconnect any tubing or connectors. The bag support housing 530 may be constructed of a variety of materials known in the art, but will preferably be constructed of either a metal, such as stainless steel, or a solid plastic, such as Plexiglas™ or acrylic. A drive assembly rotates the bag support assembly 530 so that the axis of the bag support assembly and its contained bags is horizontal.

Second culture chamber 546 also utilizes a disposable flexible bag 547, mounted within the support housing 530 between its outlet end bulkhead 538b and its second internal diaphragm 536b. The material of the outer wall of bag 547 is similar or identical to that of bag 520. The bag ends 550 and 580 are supported by central bores 533c and 533d in the internal diaphragm 536b and the bulkhead 538b, respectively. During fabrication of the second bag, the ends of the bag 547 are sealingly fused to the external cylindrical surfaces of the inlet 550 and outlet 580 bag ends by welds 590.

To assist in mixing the fluid in the bag assembly 546, one or more optional perfusion tubes are incorporated into the bag assembly. For example, two types of perfusion tubes 548 and 549 are shown in FIG. 12. These perfusion tubes are used for the purpose of introducing nutrients into the interior volume of second bioreactor chamber 545. In the cross-sectional view of FIG. 12, two attached outer perfusion tubes 548 are mounted on the interior of the bag wall. Each outer perfusion tube 548 is supported over its length, beginning a small distance from the inlet plenum 551 of inlet bag end 550, by being joined integrally with a lapped bag seam. The perfusion tube 548 is symmetrically positioned in the seam and fused to the wall of bag 547 by welds on each side of seam. The weld joints only cover a portion of the circumference of the outer perfusion tubes 548, so that a substantial portion of the tubes is still exposed to the interior volume of the bag 547.

The bag 547 may also have one or more cantilevered internal perfusion tubes 549 of various configurations as seen in FIGS. 9, 10 and 12. For example the perfusion tubes 549, shown in FIG. 12, extend from the inlet transverse end cap 558 into the interior space 545 of the bag 547. The internal perfusion tubes 548 and 549 will vary in length, weight and flexibility, depending on the viscosity of the media. The internal perfusion tubes 548 and 549 move with the rotation of the bag support 530, thus adding to the mixing of the media within the bag.

Each perfusion tube 548 and 549 has a distal closure 560 where the perfusion tube is closed or sealed by crimping and/or fusing. In contrast, the inlet end of each perfusion tube 548 and 549 is in communication with the fluid inlet plenum 551 for the bag assembly 546. The material of construction of perfusion tubes 548 and 549 is a biologically-compatible, non-toxic, non-protein-absorbing, flexible polymer having a number of perforations or a controlled permeability for the nutrient fluids for the biological media of the second chamber 545, allowing fresh media to be pumped into the bag assembly 546 under a low pressure gradient, similar to a soaker hose used in watering lawns.

The exterior of the body of inlet bag end 550 is a relatively thin walled right circular cylinder that is sized to have a slip fit within the central bore of the bag support closure 530 or within the central bore of the hinged bag support assembly. On the interior end of inlet bag end 550 is the integral thin disk inlet end cap 558, while on the exterior end of inlet bag end 550 is thin integral planar annular ring 559. Inlet end cap 558, annular ring 559, and the interior of the cylinder of inlet bag end 550 form inlet plenum 551. Concentrically attached to the exterior side of annular ring 559 of inlet bag end 550 is cylindrical inlet neck 552. The through bore 553 of inlet neck contains, in order from its external end, an annular latching groove detent engagable with the latching shoulder of connecting neck 506 of the first chamber and a female O-ring groove mounting an O-ring. The bore 553 is a close fit to the cylindrical exterior of connecting neck 506, thereby permitting the O-ring in the cylindrical inlet neck 552 to seal to connecting neck 506.

Radial secondary inlet hose barb 554 has concentric interior through barb bore 555 that penetrates the bore 553 in the interior of inlet neck 552. The downstream end of secondary flow tube 461 is attached to inlet hose barb 554, thereby permitting comingling of the outlet flow stream from the first chamber 501 and the secondary nutrient flow for the second chamber 546. The commingled flow stream freely passes to the inlet plenum 551 for distribution into the interior 545 of the bag 547 through the tubes 548 and 549.

Multiple radial branch ports extend through the cylindrical wall of inlet bag end 550 and intersect inlet plenum 551. An attached outer perfusion tube 548 is fused into each branch port so that the bore of each tube 548 is in communication with inlet plenum 551. Likewise, multiple interior perfusion tubes 549 are fused into corresponding branch ports that are provided in inlet end cap 558 coplanar with and at an angle ranging from 0° to 45° to the axis of the inlet end cap. Each cantilevered interior perfusion tube 549 thus has its bore in communication with inlet plenum 551.

Outlet bag end 580 is a right circular cylinder that has a coaxial flat bottom counterbore 581 in its interior transverse end and a connecting neck 582 for a fluid swivel 50 (not shown) that conveys the outflow from the second chamber 546 to storage or processing. Connecting neck functionally is substantially similar to connecting neck 506 of the first chamber 501. Concentric through bore 583 passes through neck 582 and intersects counterbore 581.

Controlled porosity cylindrical filter disk 586, which has a thickness less than the depth of counterbore 581, is sealingly mounted externally flush in counterbore 581, thereby creating collector plenum 587 between the filter disk 586 and the counterbore 581. Outflow fluid emerging from the second chamber 546 is filtered by disk 586 to prevent the cells within the second chamber from leaving that chamber, while at the same time waste products and the desired output products produced within second chamber 546 are passed by filter disk 586.

EXAMPLE 9

Interconnected Disposable Culture Chambers

Figure 13:
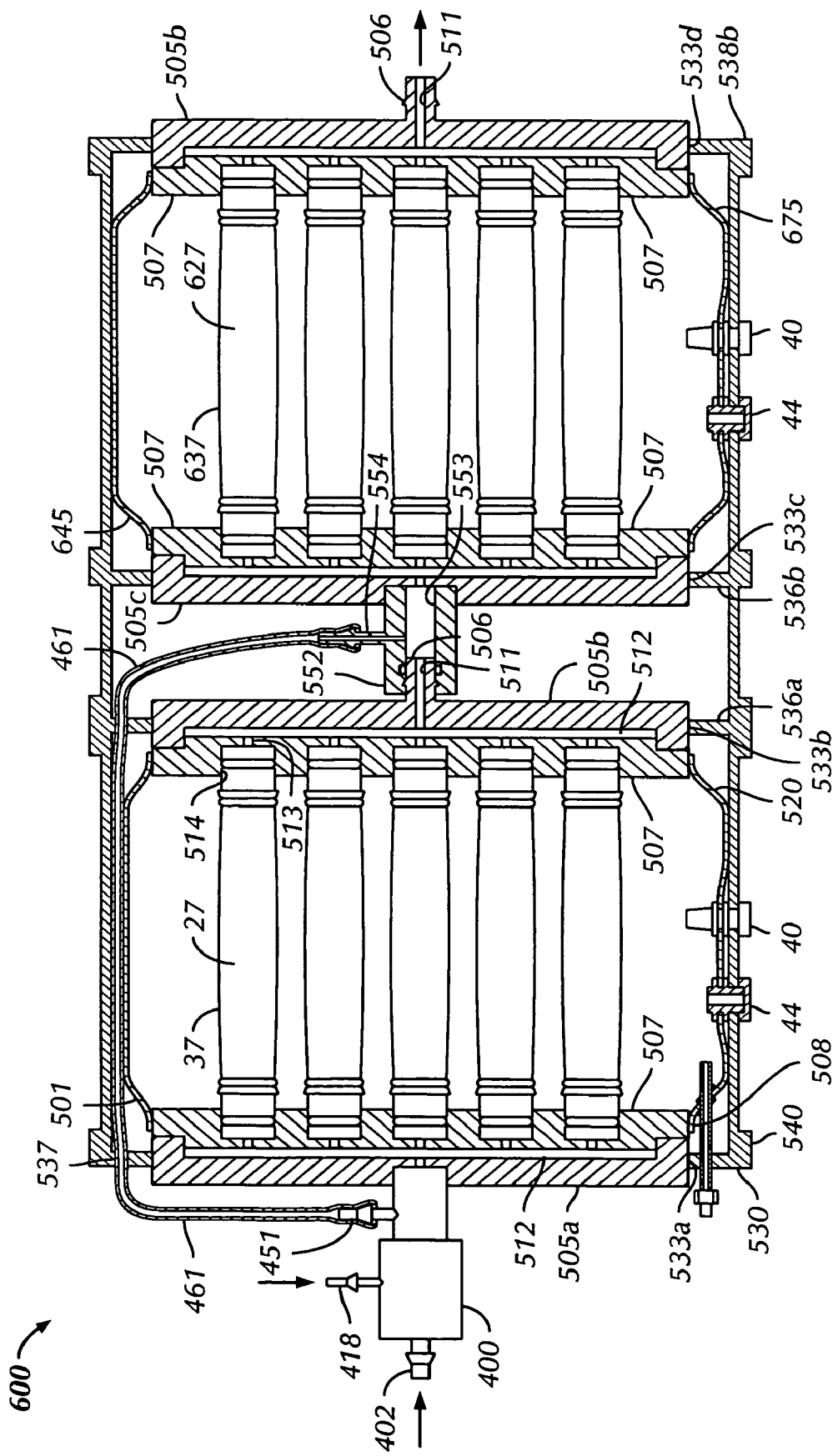
FIG. 13 is a longitudinal cross-sectional view of another tandem bioreactor system wherein flexible disposable bioreactor chambers are mounted in tandem within a clamshell housing.

FIG. 13 shows a bioreactor system 600 having serially arranged biological culture chambers 602 and 645. The bioreactor system 600 is similar in several ways to the bioreactor system 500 and uses several common components. However, rather than using a second chamber bag with the perfusion tubes disclosed in FIG. 10, the bioreactor system 600 uses bags with multiple interior membrane carrier assemblies 27 or components substantially similar to the membrane carrier assemblies 27 for both the first chamber 602 and the second chamber 645.

Referring to FIG. 13, the bag assembly 501 constituting the first chamber 602 includes bag 520 that has two similar end pieces 505*a* and 505*b* for establishing fluid interconnections and positioning the bag assembly 501. The bag assembly 501 of the system 600 is configured to mount multiple membrane carrier assemblies 27 in an array symmetrical about the longitudinal axis of bag 520. Bag assembly 501 includes multiple service ports such as a gas venting port 44 and a fill port 40. The bag assembly 501 has its constituent components welded or bonded or fused together. Furthermore, all of the components of the bag assembly 501 contacting the biological media are biologically non-reactive, non-toxic and exhibit low protein binding properties.

Outlet side bag end 505*b* is a right circular cylindrical disk having a concentric connecting neck 506 on its outer transverse face. Flanged disk 507 has a thin outer flange which has the same outer diameter as bag end 505*b* and a main cylindrical body which is a close fit to the bore of cavity 512 and is bonded thereto, thereby closing cavity 512. The outer side of disk 507 that is exposed to the interior of bag assembly 501 has an array of multiple regularly spaced flat bottom counterbores 514. The array of counterbores 514 may be placed in a hexagonal pattern or in multiple hole circles and may include a counterbore on the axis of bag end 505*b*, as shown in FIG. 13. Each counterbore 514 is intercepted by its short coaxial hole 513 that penetrates into cavity 512. Outlet bag end 505*b* is circumferentially welded or otherwise fused at 508 on its outer cylindrical face to the corresponding end of bag 520 at its end opening. Both the bag ends 505*a,b* are aligned so that their counterbores 514 are coaxial prior to attachment to the bag 520.

Bag end 505*a* is substantially identical to bag end 505*b*, except that instead of having a connecting neck 506, a short axially positioned flat bottom counterbore is provided in the outer end of bag end 505*a* and swivel 400 is bonded therein, as shown in FIG. 13. This counterbore intersects hole 511, so that an inlet flow path is thereby established.

The membrane carrier assembly 27 transversing the bag assembly 501 has been previously described and is shown in detail in FIG. 3. Each of the carrier assemblies 27 has its ends slipped into and bottomed in the comating counterbores 514 on the interior faces of the bag ends 505*a,b*. Bag assembly 501 has inlet fluid coupling swivel joint 400, shown in detail in FIG. 9, to allow the bag assembly 501 to freely rotate along with its bag support housing 530 while connected to the primary input fluid feed tubing (not shown) which is attached to hose barb 402. Swivel joint 400 is also attached to a secondary fluid input stream supply tube (not shown) that is connected to hose barb 451 of the swivel. The core piece 440 of swivel 400 is axially mounted in a counterdrilled flat bottom hole on the exterior side of bag end 505*a*.

The bag support housing 530 is basically the same unit as used for the bioreactor system 500 and described above. The bag support housing 530 is a circular cylinder having transverse end bulkheads 538*a,b* and provided with two internal diaphragms 536*a,b* that serve to support the outlet and inlet ends of the first 602 and second 645 culture chambers, respectively. An axial gap is provided between the internal diaphragms 536*a,b* of bag support housing 530 for providing space for the interconnections between the first and second culture chamber bags.

Bag support housing 530 has a diametrical split so that it is divided into a top portion and a bottom portion, where the top and bottom portions are hinged together on one cylindrical side of the diametrical split and a latch is provided on the opposed side of the diametrical split. The hinge allows the top portion and the bottom portion of the bag support assembly 530 to be selectably opened and closed. Central concentric bores 533*a,b,c,d* are located in both the transverse inlet and outlet bulkhead ends 538*a,b* and central diaphragms 536*a,b* of the bag support assembly 530 and are designed to fit in the external annular grooves around the bag ends 505*a,b* and the bag ends 505*c,d* for the second culture chamber bag 645, while additional offset bores are located on the diametrical split so that they can readily accommodate insertion of fill ports into the split bore. One or more additional radial ports with clearance to permit insertion of a corresponding number of gas removal ports are appropriately positioned in the cylindrical walls of the upper and lower portions of the bag support housing 530.

A pair of coaxial holes 537 are located parallel to the axis of housing 530 and offset from the axis of the housing so that they are tangent to the inner wall of the housing. These holes 537 serve to accommodate secondary fluid delivery hose 461, which is attached to hose barb 451 and bypasses the first bioreactor chamber in bag assembly 501 so that the secondary fluid can be delivered to the second bioreactor chamber bag assembly 645. Bag assembly 501 presses secondary fluid delivery hose 461 against the interior wall of housing 530 when the bag is filled, but the hose 461 is not collapsed. Additionally, annular external tires 540 having cylindrical outer surfaces are provided on the exterior of bag support housing 530 to facilitate driving the housing by means of the external rotational drive system (not shown). The drive assembly rotates the bag support assembly 530 so that the axis of the bag support assembly and its contained bags is horizontal.

The second bioreactor chamber 645 also utilizes a disposable flexible bag assembly identical to that of bag assembly 501 except for two modifications. The first modification is that the bag 675 may have a different volume than the first bag assembly 501. This may be accomplished by making the bag 645 longer and fitting it with longer membrane carrier assemblies 627 that mount different molecular cutoff membranes 637. The second modification to second chamber 645 is that the inlet swivel 400 of the first bag assembly 501 is replaced by an inlet neck 552 which is suitable for connection to both outlet connecting neck 506 of bag assembly 501 and to the secondary supply tube 461. In order to mount inlet neck 552 for second chamber 645, the upstream bag end piece 505*c* is made identically to bag end piece 505*a* of bag assembly 501 except that the coaxial counterbore on the exterior flat face is made larger.

The second bioreactor chamber 645 is also mounted coaxially within the support housing 530 between its outlet end bulkhead 538*b* and its second internal diaphragm 536*b*. The bag ends 505*c,b* of the second chamber 645 are supported by central bores 533*c* and 533*d* in the internal diaphragm 536*b* and the bulkhead 538*b*, respectively.

Concentrically sealingly attached to the exterior side of inlet bag end 505*c* of second chamber 645 is cylindrical inlet neck 552. The through bore 553 of inlet neck contains, in order from its external end, an annular latching groove detent engagable with the latching shoulder of connecting neck 506 of first bag assembly 501 and a female O-ring groove mounting an O-ring. The bore 553 is a close fit to the cylindrical exterior of connecting neck 506, thereby permitting the O-ring in the cylindrical inlet neck 552 to seal to connecting neck 506.

Radial secondary inlet hose barb 554 has concentric interior through barb bore 555 that penetrates to the bore 553 in the interior of inlet neck 552. The downstream end of secondary flow tube 461 is attached to inlet hose barb 554, thereby permitting comingling of the outlet flow stream from the interior of the first chamber 502 and the secondary nutrient flow for the second chamber 545. The commingled flow stream freely passes to the carrier assemblies 627 for distribution into the interior of bag assembly 645.

The longer membrane carrier assemblies 627 are identical, except for their length and selection of the molecular cutoff membrane 637, to the previously described membrane carrier assemblies 27 used in the first bag assembly 501 of this embodiment and described in the disclosure of the bioreactor system 10 of the present invention. The support cylinder is made longer in its central section to support a longer membrane 637, but otherwise does not differ from the construction of cylinder 28. The material of membrane 637 may be different from that of membrane 37, in that a different molecular cut-off value may be required in order to obtain optimal disposition of the biological media and end products from the second culture chamber 645.

The operation of the first 501 and second 645 bioreactor chambers is similar to that described previously, in that the first chamber 501 contains cells supplied with the primary nutrient stream through the inlet hose barb 402 of swivel 400 and via the membrane carrier assemblies 27 mounted within chamber 501. Nutrients diffuse outwardly through the membranes 37 of carrier assemblies 27 and waste products and the desired growth hormones, precursors, stimulants, or moderator compounds diffuse inwardly through membranes 37. The outflow stream from first chamber 501 is then supplied to the inlet neck 552 of the second chamber 645 where it is commingled with the bypassed secondary nutrient stream from tube 461. The commingled stream is then supplied to the membrane carrier assemblies 627 of the second chamber 645 where its nutrients perfuse outwardly through membranes 637. The waste products from the second chamber, along with the desired products perfuse inwardly through membranes 637 and then flow out of the bioreactor system 600 through connecting neck 506 of second chamber 645, through a swivel 50 (not shown), and thence into storage or processing.

Although the present invention and its advantages have been described in detail, it should be understood that various changes, substitutions and alterations can be made herein without departing from the spirit and scope of the invention as defined by the appended claims.

What is claimed is:

1. A culture system comprising:
   (a) a fluid inlet;
   (b) a first culture compartment having a tubular housing;
   (c) a first end piece attached to the fluid inlet on one side and to a first end of the tubular housing on a second side,
   (d) a second culture compartment coaxial with the first culture compartment, the second culture compartment having a proximal end and a distal end;
   (e) a fluid connector having a first side mounted on a second end of the tubular housing and a second side mounted on the proximal end of the second culture compartment, the fluid connector having a through bore passing from the first side to the second side of the fluid connector, wherein the through bore directs a fluid stream from the first culture compartment into the second culture compartment;
   (f) a connector filter positioned on the first side of the fluid connector to filter a fluid stream passing out of the first culture compartment and into the through bore of the fluid connector;
   (g) a fluid outlet;
   (h) a distal end piece mounted on the distal end of the second culture compartment and connected to the fluid outlet; and
   (i) an outlet filter transversing the second culture compartment including:
       a support cylinder having a first end supported by the fluid connector and a second end supported by the distal end piece,
       a molecular weight cut-off membrane secured to an exterior surface of the support cylinder, and
       a chamber between the exterior surface of the cylinder and an interior surface of the membrane, the chamber in fluid communication with the through bore of the fluid connector and the fluid outlet.

2. A culture system comprising:
   (a) a fluid inlet;
   (b) a first culture compartment having a tubular housing made of a fluid-impenetrable material, wherein the tubular housing has a first end and an opposed second end;

(c) a first end piece attached to the fluid inlet on one side and to the first end of the tubular housing on a second side, (d) a second culture compartment coaxial with the first culture compartment and in fluid communication with the first culture compartment, the second culture compartment having a proximal end and a distal end;

(e) a fluid connector having a first side mounted on the second end of the tubular housing and a second side mounted on the, proximal end of the second culture compartment, the fluid connector having a through bore passing from the first side to the second side of the fluid connector;

(f) a connector filter having a first end and a second end, wherein the first end is mounted on the first side of the fluid connector, the connector filter positioned to filter a fluid stream passing out of the first culture compartment into the through bore of the fluid connector and into the second culture compartment;

(g) a fluid outlet;

(h) a distal end piece mounted on the distal end of the second culture compartment and connected to the fluid outlet; and (i) an outlet filter having a one end mounted on a proximal side of the distal end piece, wherein the outlet filter is a membrane carrier assembly transversing the second culture compartment wherein the membrane carrier assembly has:

a support cylinder;

a molecular weight cut-off membrane secured to an exterior surface of the support cylinder, and a chamber between the exterior surface of the cylinder and an interior surface of the membrane, the chamber in fluid communication with the through bore of the fluid connector and the fluid outlet.

3. The culture system of claim 2, wherein the through bore of the fluid connector is intersected by a through bore of a second fluid inlet.

4. The culture system of claim 2, further comprising at least one penetration port extending through a wall of the first or second culture compartment.

5. The culture system of claim 2, further comprising a gas venting means for allowing gas to escape from the first or second culture compartment as the compartment is filled with fluid.

6. The culture system of claim 2, further comprising a fill means for inserting fluids into or removing fluids out of the first or second culture compartment.

7. The culture system of claim 2, wherein the first end, the distal end and the fluid connector are concurrently rotated by a drive assembly.

8. The culture system of claim 2, wherein the second culture compartment has a greater volume than the first culture compartment.

9. The culture system of claim 2, further comprising an identifier.

10. The culture system of claim 9, wherein the identifier is a bar code.

11. A culture system comprising:

(a) a fluid inlet;

(b) a first culture compartment having (i) a fluid-impenetrable tubular sleeve having a first end and an opposed second end, (ii) a growth compartment within the sleeve, and (iii) a first end piece having one side attached to the fluid inlet and a second side attached to a first end of the tubular sleeve;

(c) a second culture compartment coaxial with the first culture compartment, the second culture compartment having (i) a fluid-impenetrable housing having a proximal end and a distal end; and (ii) a growth compartment within the housing that is in fluid communication with the growth compartment within the sleeve, (d) a fluid connector having a first side mounted on the second end of the tubular sleeve and a second side mounted on the proximal end of the housing, the fluid connector having a through bore passing from the first side to the second side of the fluid connector wherein the through bore is in fluid communication with the growth compartment of the first and second culture compartment;

(e) a connector filter having a one end supported by the first side of the fluid connector;

(f) a membrane carrier assembly transversing the second culture compartment comprising (i) a support cylinder, (ii) a molecular weight cut-off membrane secured to an exterior surface of the support cylinder, and (iii) a chamber between the exterior surface of the cylinder and an interior surface of the membrane, the chamber in fluid communication with the through bore of the fluid connector and the growth compartment within the housing;

(g) a fluid outlet; and (h) a distal end piece mounted on the distal end of the second culture compartment and connected to the fluid outlet.

12. The culture system of claim 11, wherein the connector filter includes a molecular weight cut-off membrane.

13. The culture system of claim 12, wherein the connector filter includes a molecular weight cut-off membrane having a different molecular weight cut-off than the molecular weight cut-off membrane of the membrane carrier assembly.

14. The culture system of claim 12, wherein the molecular weight cut-off membrane of the connector filter is identical to the molecular weight cut-off membrane of the membrane carrier assembly.

15. The culture system of claim 11, wherein the connector filter includes:

a cylindrical support transversing the first culture compartment, the support having a first end supported by the first end of the sleeve and a second end supported by the first side of the fluid connector;

a molecular weight cut-off membrane secured to an exterior surface of the cylindrical support, and a channel between the exterior surface of the cylindrical support and an interior surface of the membrane, the channel in fluid communication with the through bore of the fluid connector and the growth compartment of the first and second culture compartment.

* * * * *